United States Patent
Edwards et al.

(10) Patent No.: US 9,724,471 B2
(45) Date of Patent: Aug. 8, 2017

(54) DEVICES, SYSTEMS, AND METHODS FOR MEDICAMENT DELIVERY

(71) Applicant: kaleo, Inc., Richmond, VA (US)

(72) Inventors: Evan T. Edwards, Charlottesville, VA (US); Eric S. Edwards, Moseley, VA (US); Mark J. Licata, Doswell, VA (US)

(73) Assignee: kaleo, Inc., Richmond, VA (US)

( * ) Notice: Subject to any disclaimer, the term of this patent is extended or adjusted under 35 U.S.C. 154(b) by 476 days.

(21) Appl. No.: 14/244,311

(22) Filed: Apr. 3, 2014

(65) Prior Publication Data

US 2015/0011973 A1  Jan. 8, 2015

Related U.S. Application Data

(63) Continuation of application No. 12/818,496, filed on Jun. 18, 2010, now Pat. No. 8,690,827, which is a (Continued)

(51) Int. Cl.
*A61M 5/19* (2006.01)
*A61M 5/20* (2006.01)
(Continued)

(52) U.S. Cl.
CPC ............ *A61M 5/19* (2013.01); *A61M 5/2033* (2013.01); *A61M 5/2066* (2013.01);
(Continued)

(58) Field of Classification Search
CPC ................ A61M 2205/13; A61M 5/24; A61M 2205/18; A61M 2205/58;
(Continued)

(56) References Cited

U.S. PATENT DOCUMENTS 2,277,907 A   3/1942   Goodale, Jr. et al.
2,960,087 A   11/1960  Uytenbogaart
(Continued)

FOREIGN PATENT DOCUMENTS

AU   2004231230   6/2006
EP   1043037 A2   10/2000
(Continued)

OTHER PUBLICATIONS

"Solutions for Medical Devices," 3M Brochure, ©3M, (2006), 80-6201-3490-0, 8 pages.
(Continued)

*Primary Examiner* — Nathan R Price
*Assistant Examiner* — Melissa A Snyder

(57) ABSTRACT

Certain exemplary embodiments comprise can comprise an auto-injector, which can comprise: a vial configured to store and/or contain an injectable medicament, the vial defining a vial longitudinal axis, and a housing comprising the vial. In various embodiments, the injectable medicament can be a medicine, medication, drug, pharmaceutical, prescriptive, agent, antidote, anti-venom, hormone, stimulant, vasodilator, anesthetic, and/or nutritional supplement that is substantially ready for injection.

24 Claims, 29 Drawing Sheets

Related U.S. Application Data continuation of application No. 10/572,148, filed as application No. PCT/US2006/003415 on Feb. 1, 2006, now Pat. No. 7,749,194.

(60) Provisional application No. 60/731,886, filed on Oct. 31, 2005.

(51) Int. Cl.
  *G06F 19/00* (2011.01)
  *A61M 5/24* (2006.01)
  *A61M 5/32* (2006.01)
  *A61M 39/10* (2006.01)

(52) U.S. Cl.
  CPC ....... *G06F 19/3468* (2013.01); *A61M 5/2053* (2013.01); *A61M 5/24* (2013.01); *A61M 5/326* (2013.01); *A61M 5/3287* (2013.01); *A61M 2005/206* (2013.01); *A61M 2005/2026* (2013.01); *A61M 2005/2073* (2013.01); *A61M 2039/1083* (2013.01); *A61M 2039/1088* (2013.01); *A61M 2205/13* (2013.01); *A61M 2205/14* (2013.01); *A61M 2205/18* (2013.01); *A61M 2205/3576* (2013.01); *A61M 2205/50* (2013.01); *A61M 2205/502* (2013.01); *A61M 2205/581* (2013.01); *A61M 2205/582* (2013.01); *A61M 2205/583* (2013.01); *A61M 2205/6018* (2013.01); *A61M 2205/6036* (2013.01)

(58) Field of Classification Search
  CPC ...... A61M 2205/581; A61M 2205/583; A61M 2205/584; A61M 2205/50
  See application file for complete search history.

(56) References Cited

U.S. PATENT DOCUMENTS

| | | | |
|---|---|---|---|
| 3,055,362 | A | 9/1962 | Uytenbogaart |
| 3,115,133 | A | 12/1963 | Morando |
| 3,426,448 | A | 2/1969 | Sarnoff |
| 3,688,765 | A | 9/1972 | Gasaway |
| 3,768,472 | A | 10/1973 | Hodosh et al. |
| 3,795,061 | A | 3/1974 | Sarnoff et al. |
| 3,945,379 | A | 3/1976 | Pritz et al. |
| 4,086,062 | A | 4/1978 | Hach |
| 4,108,177 | A | 8/1978 | Pistor |
| 4,124,024 | A | 11/1978 | Schwebel et al. |
| 4,149,394 | A | 4/1979 | Sornes |
| 4,226,235 | A | 10/1980 | Sarnoff et al. |
| 4,258,713 | A | 3/1981 | Wardlaw |
| 4,360,019 | A | 11/1982 | Portner et al. |
| 4,424,057 | A | 1/1984 | House |
| 4,441,629 | A | 4/1984 | Mackal |
| 4,484,910 | A | 11/1984 | Sarnoff et al. |
| 4,573,976 | A | 3/1986 | Sampson et al. |
| 4,596,556 | A | 6/1986 | Morrow et al. |
| 4,610,666 | A | 9/1986 | Pizzino |
| 4,613,328 | A | 9/1986 | Boyd |
| 4,617,557 | A | 10/1986 | Gordon |
| 4,624,660 | A | 11/1986 | Mijers et al. |
| 4,640,686 | A | 2/1987 | Dalling et al. |
| 4,643,721 | A | 2/1987 | Brunet |
| 4,666,430 | A | 5/1987 | Brown et al. |
| 4,673,657 | A | 6/1987 | Christian |
| 4,689,042 | A | 8/1987 | Sarnoff |
| 4,693,708 | A | 9/1987 | Wanderer et al. |
| 4,781,697 | A | 11/1988 | Slaughter |
| 4,782,841 | A | 11/1988 | Lopez |
| 4,784,652 | A | 11/1988 | Wikström |
| 4,795,433 | A | 1/1989 | Sarnoff |
| 4,822,340 | A | 4/1989 | Kamstra |
| 4,826,489 | A | 5/1989 | Haber |
| 4,853,521 | A | 8/1989 | Claeys et al. |
| 4,865,582 | A | 9/1989 | Sibalis |
| 4,874,382 | A | 10/1989 | Lindemann et al. |
| 4,894,054 | A | 1/1990 | Miskinyar |
| 4,906,235 | A | 3/1990 | Roberts |
| 4,915,695 | A | 4/1990 | Koobs |
| 4,941,880 | A | 7/1990 | Burns |
| 4,959,056 | A | 9/1990 | Dombrowski et al. |
| 4,968,302 | A | 11/1990 | Schluter et al. |
| 4,983,164 | A | 1/1991 | Hook et al. |
| 5,000,736 | A | 3/1991 | Kaufhold, Jr. et al. |
| 5,024,656 | A | 6/1991 | Gasaway et al. |
| 5,037,306 | A | 8/1991 | van Schoonhoven |
| 5,038,023 | A | 8/1991 | Saliga |
| 5,041,088 | A | 8/1991 | Ritson et al. |
| 5,042,977 | A | 8/1991 | Bechtold et al. |
| 5,062,603 | A | 11/1991 | Smith et al. |
| 5,064,413 | A | 11/1991 | McKinnon et al. |
| 5,071,353 | A | 12/1991 | van der Wal |
| 5,085,642 | A | 2/1992 | Sarnoff et al. |
| 5,092,843 | A | 3/1992 | Monroe et al. |
| 5,104,380 | A | 4/1992 | Holman et al. |
| 5,125,898 | A | 6/1992 | Kaufhold, Jr. et al. |
| 5,167,641 | A | 12/1992 | Schmitz |
| 5,199,949 | A | 4/1993 | Haber et al. |
| 5,224,936 | A | 7/1993 | Gallagher |
| 5,240,146 | A | 8/1993 | Smedley et al. |
| 5,271,527 | A | 12/1993 | Haber et al. |
| 5,279,514 | A | 1/1994 | Lacombe et al. |
| 5,281,198 | A | 1/1994 | Haber et al. |
| 5,286,258 | A | 2/1994 | Haber et al. |
| 5,298,023 | A | 3/1994 | Haber et al. |
| 5,312,326 | A | 5/1994 | Myers et al. |
| 5,314,412 | A | 5/1994 | Rex |
| 5,314,502 | A | 5/1994 | McNichols et al. |
| 5,343,519 | A | 8/1994 | Feldman |
| 5,344,407 | A | 9/1994 | Ryan |
| 5,354,284 | A | 10/1994 | Haber et al. |
| 5,356,376 | A | 10/1994 | Milijasevic et al. |
| 5,363,842 | A | 11/1994 | Mishelevich et al. |
| 5,380,281 | A | 1/1995 | Tomellini et al. |
| 5,383,851 | A | 1/1995 | McKinnon, Jr. et al. |
| 5,383,864 | A | 1/1995 | van den Heuvel |
| 5,394,866 | A | 3/1995 | Ritson et al. |
| 5,399,163 | A | 3/1995 | Peterson et al. |
| 5,417,660 | A | 5/1995 | Martin |
| 5,466,217 | A | 11/1995 | Myers et al. |
| 5,505,192 | A | 4/1996 | Samiotes et al. |
| 5,514,135 | A | 5/1996 | Earle |
| 5,540,664 | A * | 7/1996 | Wyrick ............. A61M 5/002 604/135 |
| 5,558,679 | A | 9/1996 | Tuttle |
| 5,567,160 | A | 10/1996 | Massino |
| 5,568,555 | A | 10/1996 | Shamir |
| 5,569,192 | A | 10/1996 | van der Wal |
| 5,584,815 | A | 12/1996 | Pawelka et al. |
| 5,610,992 | A | 3/1997 | Hickman |
| 5,615,771 | A | 4/1997 | Hollister |
| 5,616,132 | A | 4/1997 | Newman |
| 5,642,731 | A | 7/1997 | Kehr |
| 5,645,534 | A | 7/1997 | Chanoch |
| 5,662,612 | A | 9/1997 | Niehoff |
| 5,681,291 | A | 10/1997 | Galli |
| 5,692,492 | A | 12/1997 | Bruna et al. |
| 5,695,476 | A | 12/1997 | Harris |
| 5,697,916 | A | 12/1997 | Schraga |
| 5,716,338 | A | 2/1998 | Hjertman et al. |
| 5,728,074 | A | 3/1998 | Castellano et al. |
| 5,740,794 | A | 4/1998 | Smith et al. |
| 5,752,235 | A | 5/1998 | Kehr et al. |
| 5,772,635 | A | 6/1998 | Dastur et al. |
| 5,792,190 | A | 8/1998 | Olson et al. |
| 5,800,397 | A | 9/1998 | Wilson et al. |
| 5,805,423 | A | 9/1998 | Wever et al. |
| 5,809,997 | A | 9/1998 | Wolf |
| 5,813,397 | A | 9/1998 | Goodman et al. |
| 5,814,020 | A | 9/1998 | Gross |
| 5,823,346 | A | 10/1998 | Weiner |
| 5,832,488 | A | 11/1998 | Eberhardt |

(56) References Cited

U.S. PATENT DOCUMENTS

| | | |
|---|---|---|
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,868,713 A | 2/1999 | Klippenstein |
| 5,868,721 A | 2/1999 | Marinacci |
| D407,487 S | 3/1999 | Greubel et al. |
| 5,925,021 A | 7/1999 | Castellano et al. |
| 5,928,195 A | 7/1999 | Malamud |
| 5,941,857 A | 8/1999 | Nguyen et al. |
| 5,954,641 A | 9/1999 | Kehr et al. |
| 5,964,739 A | 10/1999 | Champ |
| 5,970,457 A | 10/1999 | Brant et al. |
| 5,971,953 A | 10/1999 | Bachynsky |
| 5,991,655 A | 11/1999 | Gross et al. |
| 6,002,781 A | 12/1999 | Takayama et al. |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,144,310 A | 11/2000 | Morris |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,175,752 B1 | 1/2001 | Say |
| 6,179,812 B1 | 1/2001 | Botich et al. |
| 6,190,326 B1 | 2/2001 | McKinnon et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,249,717 B1 | 6/2001 | Nicholson et al. |
| 6,258,063 B1 | 7/2001 | Haar et al. |
| 6,259,654 B1 | 7/2001 | de la Huerga |
| 6,264,629 B1 | 7/2001 | Landau |
| 6,270,455 B1 | 8/2001 | Brown |
| 6,285,757 B1 | 9/2001 | Carroll et al. |
| 6,312,412 B1 | 11/2001 | Saied et al. |
| 6,317,630 B1 | 11/2001 | Gross et al. |
| 6,321,070 B1 | 11/2001 | Clark et al. |
| 6,321,654 B1 | 11/2001 | Robinson |
| 6,323,780 B1 | 11/2001 | Morris |
| 6,334,070 B1 | 12/2001 | Nova et al. |
| 6,364,866 B1 | 4/2002 | Furr et al. |
| 6,371,939 B2 | 4/2002 | Bergens et al. |
| 6,377,848 B1 | 4/2002 | Garde et al. |
| 6,387,078 B1 | 5/2002 | Gillespie, III |
| 6,398,760 B1 | 6/2002 | Danby |
| 6,405,912 B2 | 6/2002 | Giannou |
| 6,411,567 B1 | 6/2002 | Niemiec et al. |
| 6,413,236 B1 | 7/2002 | Van Dyke |
| 6,425,897 B2 | 7/2002 | Overes et al. |
| 6,428,517 B1 | 8/2002 | Hochman et al. |
| 6,428,528 B2 | 8/2002 | Sadowski |
| 6,475,181 B1 | 11/2002 | Potter et al. |
| 6,478,769 B1 | 11/2002 | Parker |
| 6,478,771 B1 | 11/2002 | Lavi et al. |
| 6,482,185 B1 | 11/2002 | Hartmann |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,539,281 B2 | 3/2003 | Wan et al. |
| 6,540,672 B1 | 4/2003 | Simonsen et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,560,471 B1 | 5/2003 | Heller |
| 6,565,533 B1 | 5/2003 | Smith et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,597,794 B2 | 7/2003 | Cole et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,659,980 B2 | 12/2003 | Moberg et al. |
| 6,679,862 B2 | 1/2004 | Diaz et al. |
| 6,689,093 B2 | 2/2004 | Landau |
| 6,702,778 B2 | 3/2004 | Hill et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,764,469 B2 | 7/2004 | Broselow |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,805,686 B1 | 10/2004 | Fathallah et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,923,764 B2 | 8/2005 | Aceti et al. |
| 6,936,029 B2 | 8/2005 | Mann et al. |
| 6,936,032 B1 | 8/2005 | Bush, Jr. et al. |
| 6,937,150 B2 | 8/2005 | Medema et al. |
| 6,942,646 B2 | 9/2005 | Langley et al. |
| 6,945,961 B2 | 9/2005 | Miller et al. |
| 6,946,299 B2 | 9/2005 | Neel et al. |
| 6,949,082 B2 | 9/2005 | Langley et al. |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,963,280 B2 | 11/2005 | Eskildsen |
| 6,964,650 B2 | 11/2005 | Alexandre et al. |

(56) References Cited

U.S. PATENT DOCUMENTS

| | | |
|---|---|---|
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,072,738 B2 | 7/2006 | Bonney et al. |
| 7,074,211 B1 * | 7/2006 | Heiniger ............... A61M 5/326 604/117 |
| 7,093,595 B2 | 8/2006 | Nesbitt |
| 7,104,972 B2 | 9/2006 | Moller et al. |
| 7,113,101 B2 | 9/2006 | Peterson et al. |
| 7,116,233 B2 | 10/2006 | Zhurin |
| 7,118,553 B2 | 10/2006 | Scherer |
| 7,126,879 B2 | 10/2006 | Snyder |
| 7,158,011 B2 | 1/2007 | Brue |
| 7,191,916 B2 | 3/2007 | Clifford et al. |
| 7,229,458 B2 | 6/2007 | Boecker et al. |
| 7,278,983 B2 | 10/2007 | Ireland et al. |
| 7,299,981 B2 | 11/2007 | Hickle et al. |
| 7,343,914 B2 | 3/2008 | Abrams et al. |
| 7,351,223 B2 | 4/2008 | Call |
| 7,416,540 B2 | 8/2008 | Edwards et al. |
| 7,544,188 B2 | 6/2009 | Edwards et al. |
| 7,648,482 B2 | 1/2010 | Edwards et al. |
| 7,648,483 B2 | 1/2010 | Edwards et al. |
| 7,682,155 B2 | 3/2010 | Raven et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,850,662 B2 | 12/2010 | Veasey et al. |
| 7,871,393 B2 | 1/2011 | Monroe |
| 7,918,832 B2 | 4/2011 | Veasey et al. |
| 7,938,802 B2 | 5/2011 | Bicknell et al. |
| 7,947,017 B2 | 5/2011 | Edwards et al. |
| 8,021,344 B2 | 9/2011 | Edwards et al. |
| 8,123,719 B2 | 2/2012 | Edwards et al. |
| 8,149,111 B2 | 4/2012 | Monroe |
| 8,172,082 B2 | 5/2012 | Edwards et al. |
| 8,206,360 B2 | 6/2012 | Edwards et al. |
| 8,212,658 B2 | 7/2012 | Monroe |
| 8,226,610 B2 | 7/2012 | Edwards et al. |
| 8,231,573 B2 | 7/2012 | Edwards et al. |
| 8,424,517 B2 | 4/2013 | Sutherland et al. |
| 8,544,645 B2 | 10/2013 | Edwards et al. |
| 8,556,865 B2 | 10/2013 | Krulevitch et al. |
| 8,556,867 B2 | 10/2013 | Krulevitch et al. |
| 8,622,973 B2 | 1/2014 | Edwards et al. |
| 8,690,827 B2 | 4/2014 | Edwards et al. |
| 8,899,987 B2 | 12/2014 | Edwards et al. |
| 8,926,594 B2 | 1/2015 | Edwards et al. |
| 2001/0005781 A1 | 6/2001 | Bergens et al. |
| 2002/0072784 A1 | 6/2002 | Sheppard, Jr. et al. |
| 2002/0074345 A1 | 6/2002 | Schneider et al. |
| 2002/0076679 A1 | 6/2002 | Aman |
| 2002/0090601 A1 | 7/2002 | Strupat et al. |
| 2002/0096543 A1 | 7/2002 | Juselius |
| 2002/0169439 A1 | 11/2002 | Flaherty |
| 2002/0183721 A1 | 12/2002 | Santini, Jr. et al. |
| 2003/0028145 A1 | 2/2003 | Duchon et al. |
| 2003/0040717 A1 | 2/2003 | Saulenas et al. |
| 2003/0060765 A1 | 3/2003 | Campbell et al. |
| 2003/0106824 A1 | 6/2003 | Wilmot et al. |
| 2003/0120212 A1 | 6/2003 | Dedig et al. |
| 2003/0120222 A1 | 6/2003 | Vaillancourt |
| 2003/0130853 A1 * | 7/2003 | Maire ............... A61M 5/31535 704/275 |
| 2003/0132128 A1 | 7/2003 | Mazur |
| 2003/0233070 A1 | 12/2003 | De La Serna et al. |
| 2004/0019326 A1 | 1/2004 | Gilbert et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0069667 A1 | 4/2004 | Tomellini et al. |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0210199 A1 | 10/2004 | Atterbury et al. |
| 2004/0220524 A1 | 11/2004 | Sadowski et al. |
| 2004/0225255 A1 | 11/2004 | Ono |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0055014 A1 | 3/2005 | Coppeta et al. |
| 2005/0062603 A1 | 3/2005 | Fuerst et al. |
| 2005/0088289 A1 | 4/2005 | Rochkind |
| 2005/0090781 A1 | 4/2005 | Baba et al. |
| 2005/0090782 A1 | 4/2005 | Marshall et al. |
| 2005/0134433 A1 | 6/2005 | Sweeney, II |
| 2005/0137530 A1 | 6/2005 | Campbell et al. |
| 2005/0148931 A1 | 7/2005 | Juhasz |
| 2005/0148945 A1 | 7/2005 | Chen |
| 2005/0150488 A1 | 7/2005 | Dave |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0182358 A1 | 8/2005 | Veit et al. |
| 2005/0183982 A1 | 8/2005 | Giewercer |
| 2005/0186221 A1 | 8/2005 | Reynolds et al. |
| 2005/0190941 A1 | 9/2005 | Yang |
| 2005/0192530 A1 | 9/2005 | Castellano |
| 2005/0197654 A1 | 9/2005 | Edman et al. |
| 2005/0203466 A1 | 9/2005 | Hommann et al. |
| 2005/0209569 A1 | 9/2005 | Ishikawa et al. |
| 2005/0261742 A1 | 11/2005 | Nova et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0074519 A1 | 4/2006 | Barker et al. |
| 2006/0089592 A1 | 4/2006 | Kadhiresan et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129090 A1 | 6/2006 | Moberg et al. |
| 2006/0189938 A1 | 8/2006 | Hommann et al. |
| 2006/0200077 A1 | 9/2006 | Righi et al. |
| 2006/0204939 A1 | 9/2006 | Bardsley et al. |
| 2006/0247578 A1 | 11/2006 | Arguendas et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0074722 A1 | 4/2007 | Giroux et al. |
| 2007/0100288 A1 | 5/2007 | Bozeman et al. |
| 2007/0111175 A1 | 5/2007 | Raven et al. |
| 2007/0149954 A1 | 6/2007 | Hood et al. |
| 2007/0184847 A1 | 8/2007 | Hansen et al. |
| 2007/0186923 A1 | 8/2007 | Poutiatine et al. |
| 2007/0203247 A1 | 8/2007 | Phillips et al. |
| 2007/0210147 A1 | 9/2007 | Morrone et al. |
| 2007/0213598 A1 | 9/2007 | Howard et al. |
| 2007/0233001 A1 | 10/2007 | Burroughs et al. |
| 2007/0239116 A1 | 10/2007 | Follman et al. |
| 2007/0239140 A1 | 10/2007 | Chechelski et al. |
| 2007/0260210 A1 | 11/2007 | Conroy |
| 2007/0285238 A1 | 12/2007 | Batra |
| 2008/0059133 A1 | 3/2008 | Edwards et al. |
| 2008/0111685 A1 | 5/2008 | Olson et al. |
| 2008/0160492 A1 | 7/2008 | Campbell et al. |
| 2008/0171995 A1 | 7/2008 | Vitullo et al. |
| 2008/0228143 A1 | 9/2008 | Stamp |
| 2008/0230057 A1 | 9/2008 | Sutherland |
| 2009/0030285 A1 | 1/2009 | Andersen |
| 2009/0062728 A1 | 3/2009 | Woo |
| 2009/0131875 A1 | 5/2009 | Green |
| 2009/0143761 A1 | 6/2009 | Cantor et al. |
| 2009/0194104 A1 | 8/2009 | Van Sickle |
| 2009/0240200 A1 | 9/2009 | Heneveld et al. |
| 2010/0160894 A1 | 6/2010 | Julian et al. |

(56) References Cited

U.S. PATENT DOCUMENTS

| | | |
|---|---|---|
| 2010/0169111 A1 | 7/2010 | Brue et al. |
| 2010/0192948 A1 | 8/2010 | Sutherland et al. |
| 2010/0211005 A1 | 8/2010 | Edwards et al. |
| 2010/0250280 A1 | 9/2010 | Sutherland |
| 2011/0144574 A1 | 6/2011 | Kamen et al. |
| 2011/0201999 A1 | 8/2011 | Cronenberg |
| 2011/0264033 A1 | 10/2011 | Jensen et al. |
| 2011/0295215 A1 | 12/2011 | Nielsen et al. |
| 2012/0015335 A1 | 1/2012 | Smith et al. |
| 2012/0046613 A1 | 2/2012 | Plumptre |
| 2012/0052837 A1 | 3/2012 | Reich et al. |
| 2012/0071819 A1 | 3/2012 | Bruggemann et al. |
| 2012/0079718 A1 | 4/2012 | Singer et al. |
| 2012/0101444 A1 | 4/2012 | Muller-Pathle et al. |
| 2012/0107783 A1 | 5/2012 | Julian et al. |
| 2012/0165747 A1 | 6/2012 | Lanin et al. |
| 2012/0233834 A1 | 9/2012 | Szechinski et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0271243 A1 | 10/2012 | Plumptre et al. |
| 2013/0023825 A1 | 1/2013 | Edwards et al. |
| 2013/0079725 A1 | 3/2013 | Shang |
| 2013/0110050 A1 | 5/2013 | Boyd et al. |
| 2013/0184649 A1 | 7/2013 | Edwards et al. |
| 2013/0190692 A1 | 7/2013 | Edwards et al. |
| 2013/0266919 A1 | 10/2013 | Baker et al. |
| 2013/0280687 A1 | 10/2013 | Edwards et al. |
| 2014/0031789 A1 | 1/2014 | Edwards et al. |
| 2014/0148783 A1 | 5/2014 | Edwards et al. |
| 2014/0188048 A1 | 7/2014 | Edwards et al. |
| 2014/0276385 A1 | 9/2014 | Buchine et al. |
| 2014/0296824 A1 | 10/2014 | Edwards et al. |
| 2014/0371714 A1 | 12/2014 | Edwards et al. |
| 2015/0190591 A1 | 7/2015 | Edwards et al. |
| 2015/0196711 A1 | 7/2015 | Edwards et al. |
| 2015/0302779 A1 | 10/2015 | Edwards et al. |
| 2016/0121056 A1 | 5/2016 | Edwards et al. |
| 2016/0166768 A1 | 6/2016 | Edwards et al. |
| 2016/0184535 A1 | 6/2016 | Edwards et al. |
| 2017/0049954 A1 | 2/2017 | Edwards et al. |

FOREIGN PATENT DOCUMENTS

| | | |
|---|---|---|
| EP | 1287840 A1 | 3/2003 |
| EP | 1462134 A1 | 9/2004 |
| EP | 1518575 A1 | 3/2005 |
| EP | 1712178 A2 | 10/2006 |
| GB | 2195544 A1 | 4/1988 |
| JP | 2006-034845 | 2/2006 |
| WO | WO 91/04760 | 4/1991 |
| WO | WO 93/02720 | 2/1993 |
| WO | WO 95/26009 | 9/1995 |
| WO | WO 96/25965 | 8/1996 |
| WO | WO 97/30742 | 8/1997 |
| WO | WO 98/52632 | 11/1998 |
| WO | WO 99/07425 | 2/1999 |
| WO | WO 99/10031 | 3/1999 |
| WO | WO 99/43283 | 9/1999 |
| WO | WO 01/24690 | 4/2001 |
| WO | WO 01/26020 | 4/2001 |
| WO | WO 01/41849 | 6/2001 |
| WO | WO 01/88828 | 11/2001 |
| WO | WO 01/93926 | 12/2001 |
| WO | WO 02/24257 | 3/2002 |
| WO | WO 03/057283 | 7/2003 |
| WO | WO 03/095001 | 11/2003 |
| WO | WO 03/097133 | 11/2003 |
| WO | WO 2004/041330 | 5/2004 |
| WO | WO 2005/050526 | 6/2005 |
| WO | WO 2005/077441 | 8/2005 |
| WO | WO 2006/045525 | 5/2006 |
| WO | WO 2006/085175 | 8/2006 |
| WO | WO 2006/085204 | 8/2006 |
| WO | WO 2006/109778 | 10/2006 |
| WO | WO 2006/123956 | 11/2006 |
| WO | WO 2006/125692 | 11/2006 |
| WO | WO 2007/083115 | 7/2007 |
| WO | WO 2007/088444 | 8/2007 |
| WO | WO 2008/005315 | 1/2008 |
| WO | WO 2008/008451 | 1/2008 |
| WO | WO 2008/148864 | 12/2008 |
| WO | WO 2010/114392 | 10/2010 |
| WO | WO 2013/043063 | 3/2013 |
| WO | WO 2013/044172 | 3/2013 |

OTHER PUBLICATIONS

Tingelstad, M., "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint &ArticleID=CA6332947>, 3 pages.

"Flexible circuits / Flex circuits / Flexible Technology Ltd.," Flexible Technology Limited [online] [retrieved on Aug. 28, 2006] Retrieved from the Internet <URL: http://www.flexibletechnology.com/ >, 2 pages.

"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible circuits Capability.htm>, 2 pages.

"Flex Circuits/flexible circuits design guide," [online] [retrieved on Aug. 28, 2006] Retrieved from the Internet <URL: http://flexiblecircuit.co.uk/Flex Circuits Design Guide.htm >, 7 pages.

"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >, 3 pages.

"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/product catalogue.asp >, 9 pages.

"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >, 3 pages.

Allan, R., "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>, 3 pages.

RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >, 2 pages.

"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8>, 3 pages.

Scholz, O., "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true>, 1 page.

Heartsine Technology, samaritan™ Pad Accessories [online] [retrieved on Jun. 1, 2007] Retrieved from the Internet <URL: http://www.heartsine.com/aboutsam-accessories.htm>, 4 pages.

CliniSense Corporation, "Drug delivery devices A potentially harsh environment for drugs," Stability [online] [retrieved on Jun. 1, 2007] Retrieved from the Internet <URL: http://www.clinisense.com/devices.htm>, 2 pages.

CliniSense Corporation, "LifeTrack Technology A new method to detect improper storage." Stability [online] [retrieved on Jun. 1, 2007] Retrieved from the Internet <URL: http://www.clinisense.com/tech.htm>, 2 pages.

AED Professionals™ Brochure [online] [retrieved on Jun. 1, 2007] Retrieved from the Internet <URL: http://www.aedprofessionals.com>, 4 pages.

Ruppar, D., "Implant Technologies Expected to Remain a Niche but Effective Method of Drug Delivery," Drug Delivery Technology,

(56) References Cited

OTHER PUBLICATIONS

Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8>, 8 pages.
Meridian Medical Technologies, Inc., "Pralidoxime Chloride Trainer," 2006. [retrieved on Feb. 16, 2007] Retrieved from the Internet <URL: http://www.meridianmeds.com/auto-injectors/2pamcl_trainer.html/>, 1 page.
Gosbee, L. L., "Nuts! I Can't Figure Out How to Use My Life-Saving Epinephrine Auto-Injector," Joint Commision Journal on Quality and Safety, 30(4):220-223 (Apr. 2004).
Amgen, "Using Aranesp prefilled SureClick autoinjector is a simple 3-step process," 2006. [retrieved on Feb. 16, 2007] Retrieved from the Internet <URL: http://www.aranesp.com/patient/cia/sureclick/using_three_steps.jsp/>, 4 pages.
McDougall, L., "Addicts to be given personal supply of anti-overdose drug," The Herald Scotland, May, 28, 2006. Retrieved from the Internet <URL: http://www.heraldscotland.com/sport/spl/aberdeen/addicts-to-be-given-personal-supply-of-anti-overdose-drug-heroin-controversial-lifesaving-plan-projects-aim-to-cut-rising-death-toll-by-making-naloxone-treatment-more-readily-available-1.19181>, 3 pages.
BD Accuspray™ Nasal Spray System, 2004, Retrieved from the Internet <URL: http://www.bd.com/press/pdfs/flu/bd_accuspray.pdf>, 1 page.
Office Action for Israel Patent Application No. 184552, mailed Jul. 28, 2011.
International Search Report and Written Opinion for International Patent Application No. PCT/US06/03415, mailed Jul. 13, 2006.
Search Report for European Patent Application No. 09150135.3, mailed Mar. 15, 2010.
Office Action for European Patent Application No. 09150135.3, mailed Jul. 11, 2011.
Combined Search and Examination Report for British Patent Application 0818178.6, mailed Dec. 1, 2008.
Examination Report for British Patent Application No. 0818178.6, mailed Mar. 23, 2009.
Examination Report for British Patent Application No. 0818178.6, mailed Jul. 9, 2009.
Examination Report for British Patent Application No. 0905194.7, mailed May 8, 2009.
Office Action for U.S. Appl. No. 10/572,148, mailed Jun. 19, 2009.
Office Action for U.S. Appl. No. 10/572,148, mailed Feb. 3, 2010.
Office Action for Canadian Patent Application No. 2,644,547, mailed Feb. 14, 2014.
Office Action for Chinese Patent Application No. 200780011264.5, mailed Mar. 28, 2013.
Office Action for Japanese Patent Application No. 2009-502964, mailed May 23, 2011.
Office Action for Japanese Patent Application No. 2009-502964, mailed May 21, 2012.
International Search Report and Written Opinion for International Patent Application No. PCT/US07/007626, mailed Sep. 29, 2008.
Search and Examination Report for British Patent Application No. 1104754.5, mailed May 18, 2011.
Office Action for U.S. Appl. No. 11/621,236, mailed Feb. 3, 2009.
Office Action for U.S. Appl. No. 11/621,236, mailed Jul. 1, 2009.
Office Action for U.S. Appl. No. 11/621,236, mailed Jan. 11, 2010.
Search and Examination Report for British Patent Application No. 1108993.5, mailed Jun. 17, 2011.
Office Action for U.S. Appl. No. 11/679,331, mailed Feb. 15, 2011.
Office Action for U.S. Appl. No. 11/671,025, mailed Sep. 8, 2011.
Office Action for U.S. Appl. No. 11/679,331, mailed May 12, 2010.
Examination Report for British Patent Application No. 1019599.8, mailed Feb. 7, 2012.
Office Action for U.S. Appl. No. 12/119,016, mailed Nov. 3, 2011.
Office Action for U.S. Appl. No. 12/794,020, mailed Oct. 25, 2011.
Office Action for U.S. Appl. No. 13/404,699, mailed Mar. 10, 2014.
Office Action for U.S. Appl. No. 13/924,037, mailed Feb. 13, 2014.
Office Action for U.S. Appl. No. 13/962,336, mailed Nov. 20, 2013.
Office Action for U.S. Appl. No. 13/962,336, mailed May 27, 2014.
Office Action for U.S. Appl. No. 14/470,165, mailed Dec. 26, 2014.
Office Action for U.S. Appl. No. 12/017,405, mailed Dec. 7, 2011.
Office Action for U.S. Appl. No. 12/615,636, mailed Jan. 25, 2012.
International Search Report and Written Opinion for International Patent Application No. PCT/US09/63983, mailed Feb. 25, 2010.
Office Action for U.S. Appl. No. 13/550,893, mailed Apr. 28, 2015.
Office Action for U.S. Appl. No. 14/470,165, mailed May 26, 2015.
Office Action for U.S. Appl. No. 14/664,426, mailed Jun. 9, 2015.
Office Action for U.S. Appl. No. 14/665,659, mailed Jun. 23, 2015.
Office Action for Canadian Patent Application No. 2,762,072, mailed Mar. 14, 2016.

* cited by examiner

FIG.16
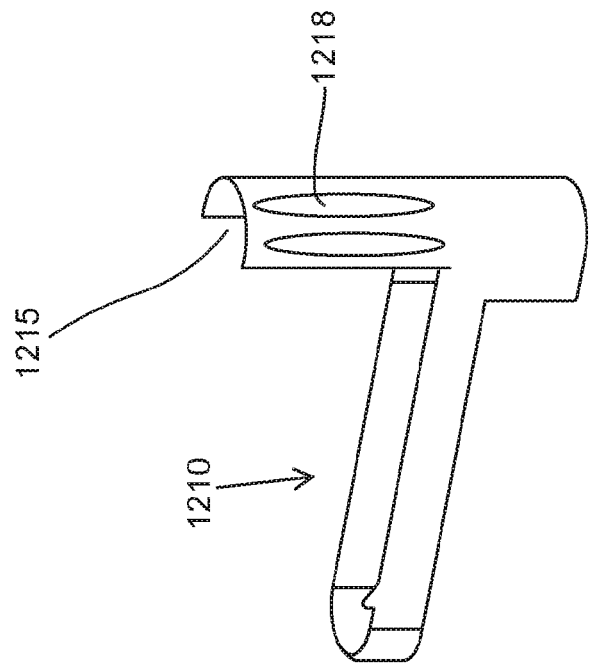
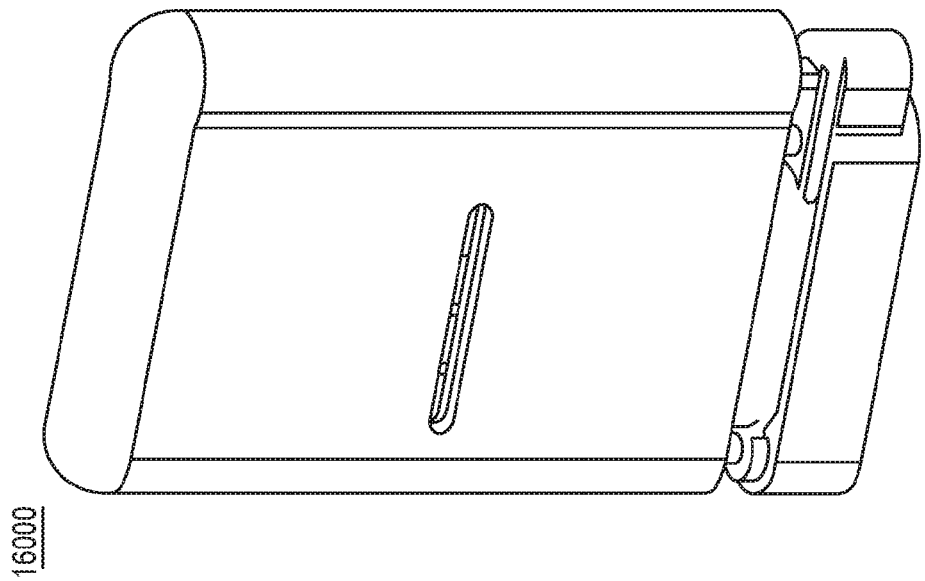

DEVICES, SYSTEMS, AND METHODS FOR MEDICAMENT DELIVERY

CROSS REFERENCES TO RELATED APPLICATIONS

This application is a continuation of U.S. patent application Ser. No. 12/818,496, entitled "Devices, Systems, and Methods for Medicament Delivery," filed Jun. 18, 2010, which is a continuation of U.S. patent application Ser. No. 10/572,148, entitled "Devices, Systems, and Methods for Medicament Delivery," filed Mar. 16, 2006 (now U.S. Pat. No. 7,749,194), which is a national stage filing under 35 U.S.C. §371 of International Patent Application No. PCT/US06/03415, entitled "Devices, Systems, and Methods for Medicament Delivery," filed Feb. 1, 2006, which claims priority to U.S. Provisional Application Ser. No. 60/731,886, entitled "Auto-injector with Feedback" filed Oct. 31, 2005, each of which is incorporated herein by reference in its entirety. International Patent Application No. PCT/US06/03415 claims priority to U.S. Provisional Application Ser. No. 60/648,822 entitled "Devices. Systems, and Methods for Medicament Delivery," filed Feb. 1, 2005, which is incorporated herein by reference in its entirety.

BRIEF DESCRIPTION OF THE DRAWINGS

A wide variety of potential embodiments will be more readily understood through the following detailed description of certain exemplary embodiments, with reference to the accompanying exemplary drawings in which:

FIG. 16 is a perspective view of an exemplary embodiment an auto-injector 16000;

DETAILED DESCRIPTION

Definitions

Figure 1:
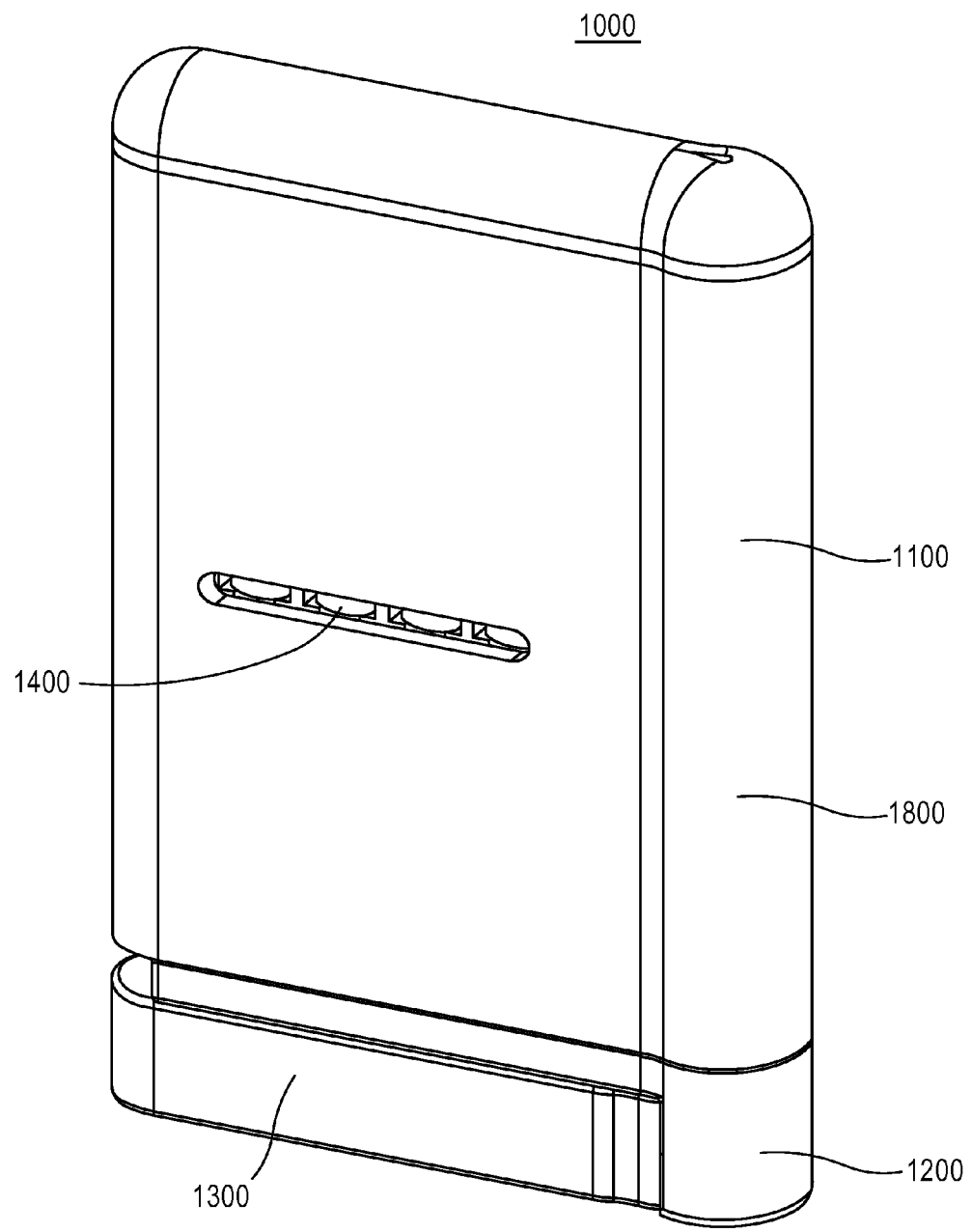
FIG. 1 is a perspective view of an exemplary embodiment of a system 1000.

When the following terms are used substantively herein, the accompanying definitions apply:

a—at least one.

activate—to actuate and/or set in motion and/or action.

activity—an action, act, step, and/or process or portion thereof.

actuating portion—that part that puts something into action.

actuation lock—a device adapted to prevent actuation, such as, for example a pivotable, translatable, keyed, squeezable, and/or removable lock.

actuator—a mechanism that puts something into action.

adapted to—suitable or fit for a particular purpose.

and/or—either in conjunction with or in alternative to.

apparatus—a mechanism and/or device.

arm—an elongated structural member, which need not be solely linear.

auto-injector—device that allows a user to deliver a medicament without having to manually prepare the injection. Exemplary devices include pen delivered injectors, syringes, needleless injectors, gas powered auto-injectors, and/or any other auto-injector and/or medical device used to inject a medicament into a user/patient, etc.

automatically—acting or operating in a manner essentially independent of external influence or control. For example, an automatic light switch can turn on upon "seeing" a person in its view, without the person manually operating the light switch.

axis—a straight line about which a body or geometric object rotates or may be conceived to rotate.

can—is capable of, in at least some embodiments.

channel—a conduit for one or more fluids.

compressed gas—a substantially pressurized substance, such as helium, nitrogen, and/or carbon dioxide, etc., in a gaseous form.

comprising—including but not limited to.

contain—to hold within.

contents—a contained compressed gas.

credit card—a card (usually plastic) that assures a seller that the person using it has a satisfactory credit rating and that the issuer will see to it that the seller receives payment for the merchandise and/or services delivered. Typically measuring in size from approximately 3 to approximately 4 inches in length, such as approximately 3.40 inches, 3.375 inches, 85 millimeters, etc., and from approximately 1.75 to approximately 2.75 inches in width, such as approximately 2.10 inches, 2.2125 inches, 2.5 inches, 55 millimeters, etc.

data—distinct pieces of information, usually formatted in a special or predetermined way and/or organized to express concepts.

define—to establish the outline, form, or structure of.

device—a machine, manufacture, and/or collection thereof.

discharge—to release from confinement; to emit.

driving force—a force sufficient to cause, directly or indirectly, expulsion of an injectable medicament from one or more vials and/or from an auto-injector.

dry substance—a material that is substantially free from liquid or moisture.

eject—to expel.

embedded system—a programmed hardware device comprising a microprocessor controlled by an operating system and/or control logic that is specifically designed for a particular kind of application. The operating system and/or control logic of an embedded system comprises a limited set of pre-defined functions that can not be modified or added to by additional user-installed software, although some embedded systems allow a user to modify values of variables and/or parameters of the pre-defined functions. Exemplary devices that can comprise embedded systems are: medical devices, calculators, automobiles, airplanes, vending machines, toys, programmable logic controllers, appliances, refrigerators, microwave ovens, clothes washers, thermostats, alarm systems, sprinkler systems, lighting controllers, electronic equipment, laser printers, CD players, DVD players, watches, and/or digital cameras, etc.

escape port—an opening for the exit of a gas.

expulsion—the act of forcibly ejecting a fluid via a designed outlet of a container.

expulsion pressure—a force applied over an area of a liquid, the force sufficient to expel the liquid in a predetermined manner.

extend—to move out and/or away from.

extendable—able to move out and/or away from.

fluid—a gas and/or liquid.

fluidly coupleable—able to be related via a fluid.

force initiator—a source, such as a compressed gas container, spring, and/or chemical reaction, etc., capable of supplying a driving force.

frangible—a device that is capable of being broken and/or penetrated to allow fluid to flow therethrough.

haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.

hard real-time—relating to computer systems that provide an absolute deterministic response to an event. Such a response is not based on average event time. Instead, in such computer systems, the deadlines are fixed and the system must guarantee a response within a fixed and well-defined time. Systems operating in hard real-time typically interact at a low level with physical hardware via embedded systems, and can suffer a critical failure if time constraints are violated. A classic example of a hard real-time computing system is the anti-lock brakes on a car. The hard real-time constraint, or deadline, in this system is the time in which the brakes must be released to prevent the wheel from locking Another example is a car engine control system, in which a delayed control signal might cause engine failure or damage. Other examples of hard real-time embedded systems include medical systems such as heart pacemakers and industrial process controllers.

hazardous condition—a situation marked by risk, danger, and/or peril.

housing—something that covers, encloses, protects, holds, and/or supports.

in reaction to—responding indirectly and/or directly to.

indicate—to show, mark, signify, denote, evidence, evince, manifest, declare, enunciate, specify, explain, exhibit, present, reveal, disclose, and/or display.

indicator—a device and/or substance that indicates.

information device—any device capable of processing information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.

injectable medicament—a medicine, medication, drug, pharmaceutical, prescriptive, agent, antidote, anti-venom, hormone, stimulant, vasodilator, anesthetic, and/or nutritional supplement that is substantially ready for injection.

input/output (I/O) device—any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.

liquid—a body of matter that exhibits a characteristic readiness to flow, little or no tendency to disperse, and relatively high incompressibility.

longitudinal—of or relating to longitude or length.

machine instructions—directions adapted to cause a machine, such as an information device, to perform a particular operation or function.

machine readable medium—a physical structure from which a machine can obtain data and/or information. Examples include a memory, punch cards, etc.

may—is allowed to, in at least some embodiments.

memory device—an apparatus capable of storing analog or digital information, such as instructions and/or data. Examples include a nonvolatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.

method—a process, procedure, and/or collection of related activities for accomplishing something.

microprocessor—an integrated circuit comprising a central processing unit.

mixable—dissolvable, dispersible, and/or capable of being put into so that the dry substance is diffused and/or commingled in the liquid.

needle—a hollow, slender, sharp-pointed instrument used for injection. Includes cannulas.

network—a communicatively coupled plurality of nodes.

network interface—any device, system, or subsystem capable of coupling an information device to a network. For example, a network interface can be a telephone, cellular phone, cellular modem, telephone data modem, fax modem, wireless transceiver, ethernet card, cable modem, digital subscriber line interface, bridge, hub, router, or other similar device.

non-co-axial—not having co-linear axes.

output device—an apparatus configured to visually, audibly, and/or haptically render information to a human. Examples include an audible output sub-system (e.g., speaker, horn, buzzer, and/or piezoelectric transducer, etc.), a visual output sub-system (e.g., flag, marker, light, liquid crystal display (LCD), light emitting diode (LED), optical fiber, organic polymer display, electric paper, screen, display, monitor, and/or tube, etc.), and a haptic output sub-system (e.g., buzzer, vibrator, bulging portion, tactile stimulator, cooler, and/or heater, etc.), etc.

patient—a receiver of an injectable medicament, such as a human, mammal, animal, etc.

piston—a sliding piece which either is moved by, or moves against, fluid pressure.

pivotable—capable of pivoting.

plurality—the state of being plural and/or more than one.

predetermined—established in advance.

processor—a device and/or set of machine-readable instructions for performing one or more predetermined tasks. A processor can comprise any one or a combination of hardware, firmware, and/or software. A processor can utilize mechanical, pneumatic, hydraulic, electrical, magnetic, optical, informational, chemical, and/or biological principles, signals, and/or inputs to perform the task(s). In certain embodiments, a processor can act upon information by manipulating, analyzing, modifying, converting, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein.

programmable logic controller (PLC)—a solid-state, microprocessor-based, hard real-time computing system that is used, via a network, to automatically monitor the status of field-connected sensor inputs, and automatically control communicatively-coupled devices of a controlled system (e.g., actuators, solenoids, relays, switches, motor starters, speed drives (e.g., variable frequency drives, silicon-controlled rectifiers, etc.), pilot lights, ignitors, speakers, tape drives, printers, monitors, displays, etc.) according to a user-created set of values and user-created logic and/or instructions stored in memory. The sensor inputs reflect measurements and/or status information related to the controlled system. A PLC provides any of: automated input/output control; switching; counting; arithmetic operations; complex data manipulation; logic; timing; sequencing; communication; data file manipulation; report generation; control; relay control; motion control; process control; distributed control; and/or monitoring of processes, equipment, and/or other automation of the controlled system. Because of its precise and hard real-time timing and sequencing capabilities, a PLC is programmed using ladder logic or some form of structured programming language specified in IEC 61131-3, namely, FBD (Function Block Diagram), LD (Ladder Diagram), ST (Structured Text, Pascal type language), IL (Instruction List) and/or SFC (Sequential Function Chart). Because of its precise and real-time timing and sequencing capabilities, a PLC can replace up to thousands of relays and cam timers. PLC hardware often has good redundancy and fail-over capabilities. A PLC can use a Human-Machine Interface (HMI) for interacting with users for configuration, alarm reporting, and/or control.

puncturer—a device adapted to penetrate using a substantially sharp and/or tapered point, tip, edge, or the like.

pusher—a device adapted to convert fluid pressure to mechanical movement.

render—make perceptible to a human, for example as data, commands, text, graphics, audio, video, animation, and/or hyperlinks, etc., such as via any visual, audio, and/or haptic means, such as via a display, monitor, electric paper, ocular implant, cochlear implant, speaker, etc.

repeatedly—again and again; repetitively.

reservoir—a receptacle or chamber for storing and/or directing movement of a fluid.

resist—to avoid and/or remain firm against the actions, effects, and/or force of.

retract—to pull inward.

safety tab—a removable device configured to prevent actuation of an auto-injector when the safety tab is in one orientation, and allow actuation when in another orientation.

sensed variable—a measured parameter.

set—a related plurality.

sheath—a protective cover.

shield—a protective device or structure.

soft real-time—relating to computer systems that take a best efforts approach and minimize latency from event to response as much as possible while keeping throughput up with external events overall. Such systems will not suffer a critical failure if time constraints are violated. For example, live audio-video systems are usually soft real-time; violation of time constraints can result in degraded quality, but the system can continue to operate. Another example is a network server, which is a system for which fast response is desired but for which there is no deadline. If the network server is highly loaded, its response time may slow with no failure in service. This is contrasted with the anti-lock braking system where a slow down in response would likely cause system failure, possibly even catastrophic failure.

spring—an elastic device, such as a coil of wire, that regains its original shape after being compressed or extended.

status—a state or condition.

store—to place, hold, and/or retain data, typically in a memory.

substantially—to a great extent or degree.

system—a collection of mechanisms, devices, data, and/or instructions, the collection designed to perform one or more specific functions.

tip—a terminal end.

transfer—to convey from one place to another.

translatable—capable of being transferred from one place to another and/or of being moved with respect to something else.

triggerable—capable of being actuated.

use indication—information regarding a use of an auto-injector, such as information regarding any of auto-injector selection; auto-injector maintenance; auto-injector expiration; auto-injector replacement; medicament expiration; medicament selection; medicament mixing; injection delay; safety guard removal; auto-injector positioning; auto-injector orientation; actuator location; injection hazard avoidance; auto-injector actuation; injection duration; injection status; injection error; auto-injector removal; auto-injector reuse; auto-injector recycling; and auto-injector disposal, etc.

user input—human-provided information.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

valve—a device that regulates flow through a pipe and/or through an aperture by opening, closing, and/or obstructing a port and/or passageway.

vent—to release from confinement.

via—by way of and/or utilizing.

vial—a closable vessel.

DETAILED DESCRIPTION

Exposure, such as via ingestion, inhalation, and/or injection, to certain allergens, toxins, and/or other substances can cause profound reactions for some and/or all people and/or animals. For example, certain people are highly allergic to certain substances, such as peanuts, shellfish, particular drugs, certain proteins, bee venom, insect bites, etc. The allergic response to the exposure can lead to anaphylactic shock, which can cause a sharp drop in blood pressure, hives, and/or substantial breathing difficulties caused by severe airway constriction. As another example, inhalation of certain nerve agents can cause severe physiological trauma. Responding rapidly to such exposures can prevent injury and/or death. For example, in response to an exposure leading to anaphylactic shock, an injection of epinephrine (i.e., adrenaline) can provide substantial and/or complete relief from the reaction. As another example, injection of an antidote to a nerve agent can greatly reduce and/or eliminate the potential harm of the exposure. As yet another example, rapid injection of certain drugs, such as a beta blocker, blood thinner, nitroglycerine, antihistamines, insulin, and opioids, etc., can provide substantial relief from various dangerous medical conditions.

Thus, certain exemplary embodiments provide systems, devices, and/or methods for rapidly injecting a medicament.

Certain exemplary embodiments comprise an apparatus, comprising: a compressed gas container; a plurality of vials adapted to store a liquid medicament, each vial defining a longitudinal axis, the longitudinal axes of the plurality of vials parallel and non-co-axial, the plurality of vials fluidly coupleable to an actuating portion of a contents of the gas container; and a plurality of pistons, each piston adapted to move within a corresponding vial from the plurality of vials, the plurality of pistons adapted to, in response to discharge of the actuating portion of the contents of the compressed gas container, transfer at least a portion of the liquid medicament from the plurality of vials and through a needle that is extendable into a patient. Certain exemplary embodiments comprise a method comprising a plurality of activities, comprising: discharging an actuating portion of a contents of a compressed gas container, the compressed gas container contained within an apparatus; in reaction to said discharging activity, moving a piston within a vial, the vial one of a plurality of vials contained within the apparatus, each vial adapted to store a liquid medicament, each vial defining a longitudinal axis, the longitudinal axes of the plurality of vials parallel and non-co-axial, the plurality of vials fluidly coupleable to a contents of the gas container; and transferring a liquid medicament from the vial and through a needle that is extendable into a patient.

Figure 2:
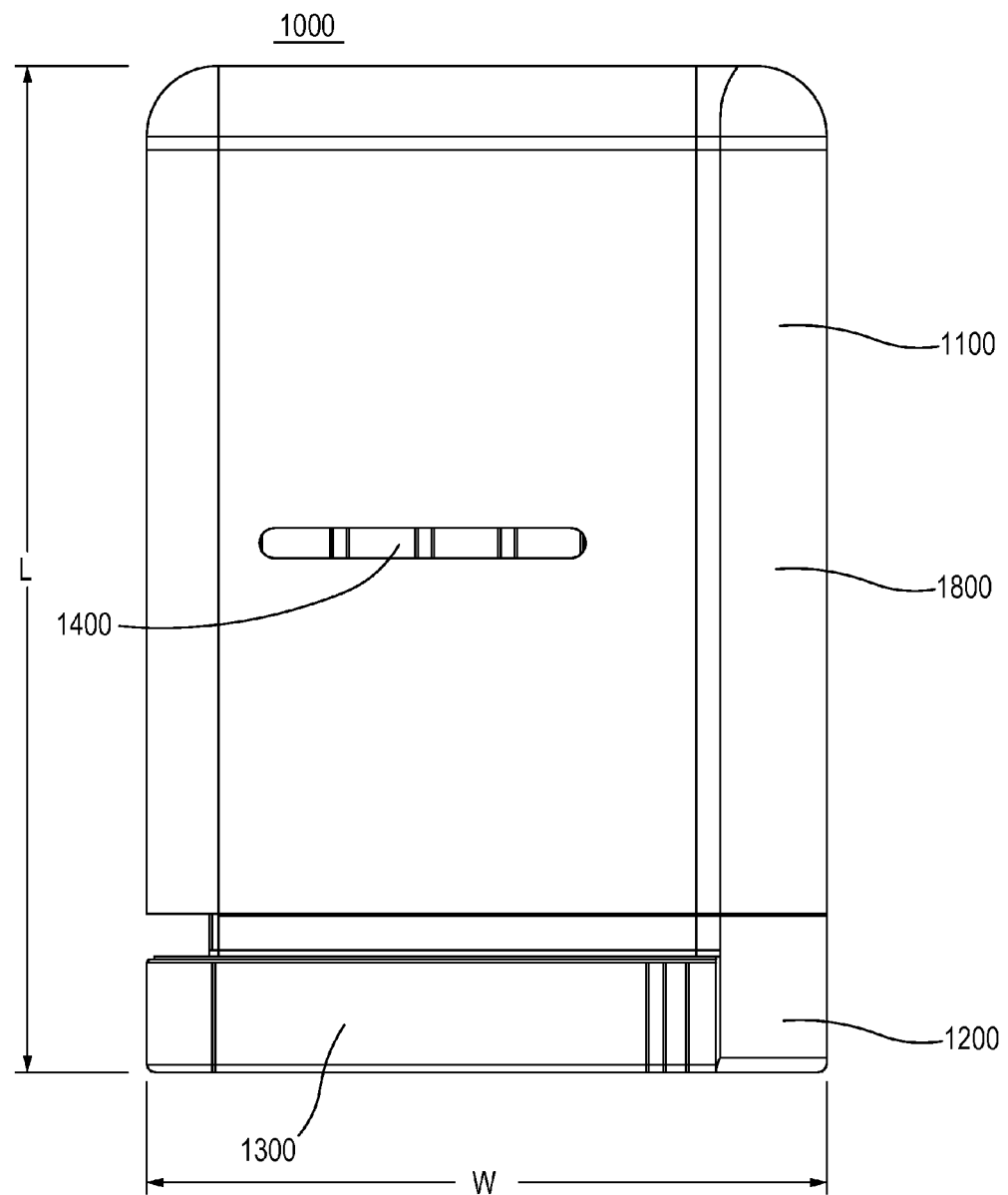
FIG. 2 is a front view of an exemplary embodiment of a system 1000.
Figure 3:
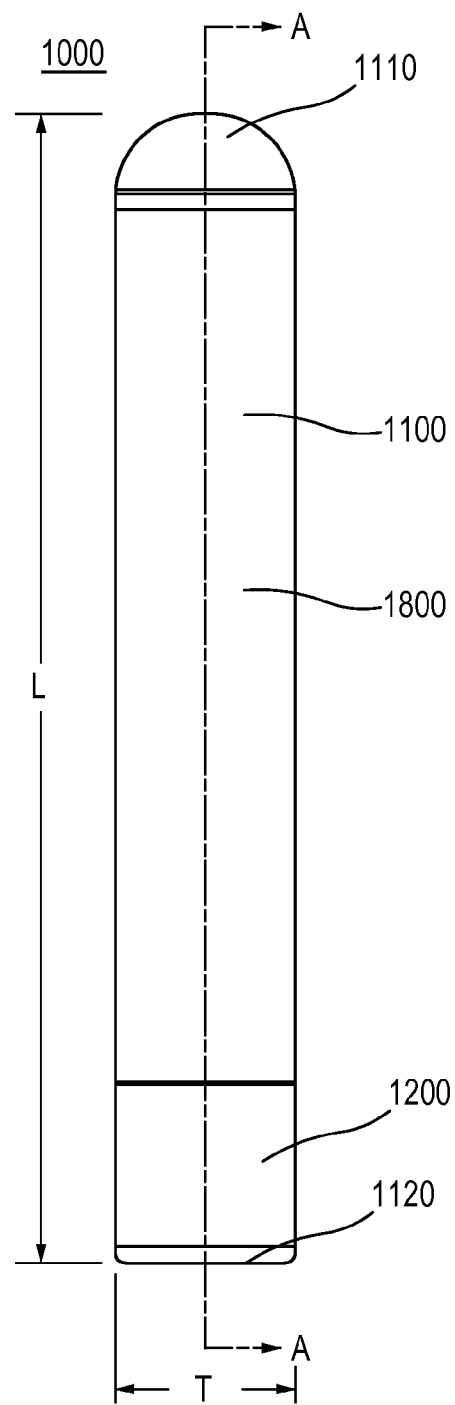
FIG. 3 is a side view of an exemplary embodiment of a system 1000.

FIG. 1 is a perspective view, FIG. 2 is a front view, and FIG. 3 is a side view, of an exemplary embodiment of a system 1000, which can comprise a housing 1100, which, in certain operative embodiments, can comprise a handheld portion 1800 separated via an actuation guard 1200 from an actuation bar 1300. Actuation guard 1200 can prevent accident activation of system 1000. Housing 1100 can be constructed of a durable material, such as stainless steel, aluminum, polycarbonate, etc., to protect a compressed gas container, medicament, injection apparatus and/or user of system 1000. The injection apparatus can be actuated by a fluid pressure, such as pressure provided by the compressed gas, which upon completion of its actuation duties can escape housing 1100 via gas escape opening, such as via status indicator 1400.

A status of a system 1000 can be determined via status indicator 1400, which can provide a view, such as via a UV blocking, photo-sensitive, and/or translucent window, into an interior of housing 1100. Viewable through the window can be a status of medicament carried by housing 1100, a location of a needle and/or injection apparatus for the medicament, and/or an activation status of system 1000. For example, if the medicament has aged to the point of discoloration, which aging might or might not render the medication useless, harmful, etc., status indicator 1400 can allow that situation to be determined. In certain exemplary embodiments, gas can escape housing 1100 via status indicator 1400 and/or another opening in housing 1100.

Certain exemplary embodiments of system 1000 can provide a compact medicament delivery mechanism that can efficiently and/or rapidly deliver a prescribed dose. The length (L) and width (W) of system 1000 can be similar to that of a credit card, and the thickness (T) can be less than one inch. Thus, certain exemplary embodiments of system 1000 can provide a conveniently carried, easy-to-use, easy to activate drug delivery apparatus that can require little to no training to safely carry, use, and/or dispose of.

To assist a user in positioning system 1000 in a correct orientation for injection, system 1000 and/or housing 1100 can provide various tactile clues. For example, a top 1110 of housing 1100 can be rounded, and a bottom 1120 of actuation bar 1300 of housing 1100 can be flat. Other tactile clues are also possible, such as bulges, ribs, grooves, gaps, roughened surfaces, indentations, etc.

Figure 4:
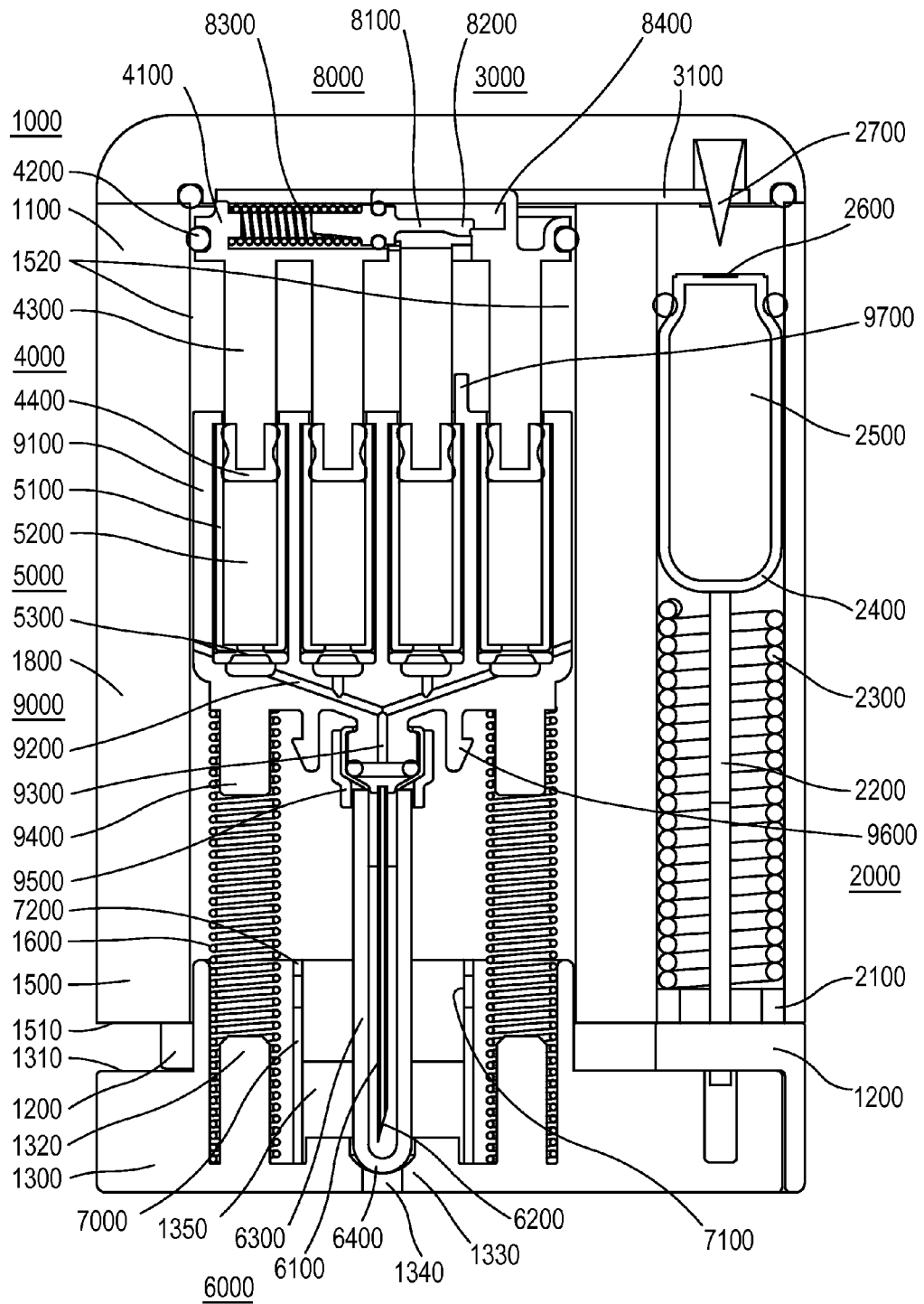
FIG. 4 is a cross-sectional view taken along lines A-A of FIG. 3 of an exemplary embodiment of a system 1000 in a first operative position.

FIG. 4 is a cross-sectional view taken along lines A-A of FIG. 3 of an exemplary embodiment of a system 1000 in a first operative position. FIGS. 5, 6, 7, 8, and 9 show system 1000 of FIG. 4 in second, third, fourth, fifth, and sixth operative positions, respectively.

System 1000 can comprise a housing 1100, handheld portion 1800, actuation guard 1200, and/or actuation bar 1300. System 1000 can comprise system actuator 2000, gas reservoirs 3000, medicament actuator 4000, medicament storage assembly 5000, medicament carrier 9000, needle assembly 6000, use indicator 7000, and/or gas vent mechanism 8000, etc.

Upon removal, release, rotation, and/or relocation of actuation guard 1200, system actuator 2000 can be adapted to rapidly discharge an actuating portion of a contents of a compress gas container. For example, system actuator 2000 can comprise a compressed gas container 2400, which initially can contain a compressed gas 2500, an actuating portion of which can be released from container 2400 by penetration of a gas port 2600 via a point of a puncturer 2700. Upon removal and/or relocation of actuation guard 1200, actuation bar 1300 can be moved closer to and/or in contact with handheld portion 1800. Upon removal and/or relocation of actuation guard 1200, gas container 2400 can be brought into contact with puncturer 2700 via extension of a pre-compressed spring 2300 and/or movement of a actuation stick 2200. Thus, actuation guard 1200 can prevent accident activation of system 1000 and/or unintended discharge of an actuating portion of the contents 2500 of gas container 2400.

Once gas port 2600 has been punctured, an actuating portion of compressed gas 2500 can escape from container 2400 and flow via gas reservoirs 3000, such as gas channel 3100. The flowing gas can meet and/or apply gas pressure to medicament actuator 4000, which can comprise a pusher 4100, which can travel within a sleeve 1500 defined by walls 1520. Sleeve 1500 can be constructed of metal, stainless steel, aluminum, plastic, polycarbonate, etc. Seals 4200, such as o-rings, can resist gas leakage, such as past pusher 4100 and/or out of housing 1100. Thus, pusher 4100 can function as a piston traveling within a cylinder, although it is not necessarily required that the cross-sectional shape of sleeve 1500 be round.

Medicament actuator 4000 can interface with medicament storage assembly 5000. For example, medicament actuator 4000 can comprise a plurality of plungers 4300, each of which can be capped with a piston 4400 which can sealingly slide and/or move within a corresponding vial 5100 containing a liquid medicament 5200. For example, in response to pressure applied by an actuating portion of the contents 2500 of compressed gas container 2400, pusher 4100 can cause plungers 4300 and/or pistons 4400 to simultaneously move. The number of corresponding sets of plungers 4300, pistons 4400, and/or vials 5100 can be 2, 3, 4, 5, 6, or more. Pistons 4400 can be constructed of a resilient, durable, and/or sealing material, such as a rubber. Each plunger 4300 from the plurality of plungers can define a longitudinal axis, the longitudinal axes (e.g., axes 4310, 4320, 4330, 4340) of the plurality of plungers parallel, non-coaxial, and/or co-planar.

Each vial 5100 from the plurality of vials can be substantially cylindrical with a substantially round and/or substantially elliptical cross-sectional shape. Thus, each vial 5100 can define a longitudinal axis, the longitudinal axes of the plurality of vials parallel, non-coaxial, and/or co-planar. The longitudinal axis of each vial can be co-axial with the longitudinal axis of its corresponding plunger.

Each vial can be capped at one end with a frangible 5300, which can be burst when piston 4400 generates sufficient pressure upon medicament 5200, thereby allowing at least a portion of medicament 5200 to flow out of vial 5100 and into medicament carrier 9000. Thus, the plurality of vials can be fluidly coupleable to the actuating portion of the contents 2500 of gas container 2400.

Medicament carrier 9000 can hold each of vials 5100 and can travel within sleeve 1500. Medicament carrier 9000 can comprise a plurality of channels 9200 adapted to receive medicament 5200 as it exits its respective vial 5100, and direct medicament 5200 to a common conduit 9300. Medicament carrier 9000 can interface with needle assembly 6000 and/or use indicator 7000.

From common conduit 9300, medicament 5200 can enter needle assembly 6000, such as into a single needle 6100 via which medicament can approach needle tip 6200. As medicament actuator 4000 and/or medicament carrier 9000 are driven toward actuator bar 1300, needle tip 6200 can penetrate an end 6400 of needle sheath 6300 and exit actuator bar 1300 at needle port 1340.

Figure 5:
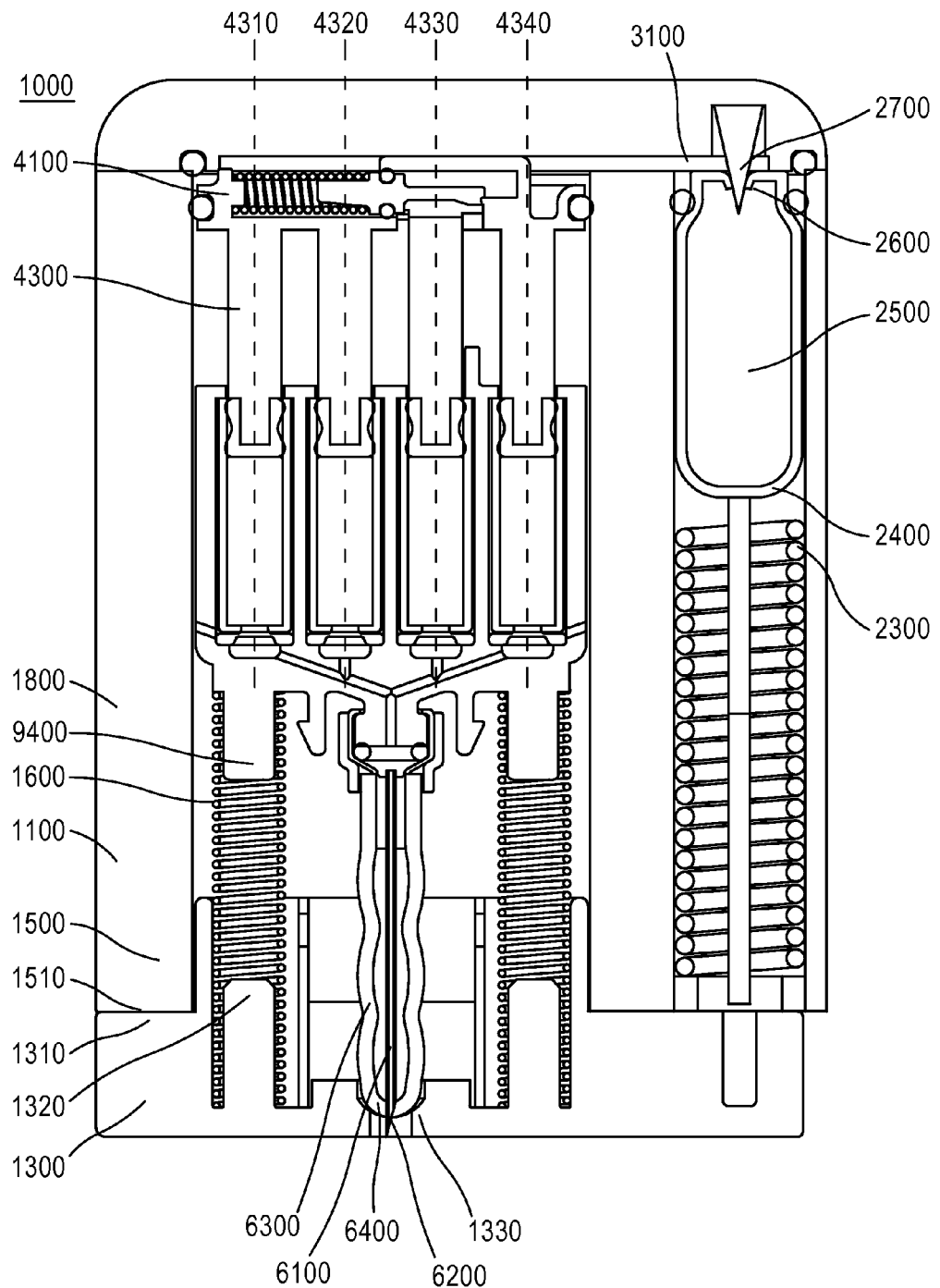
FIG. 5 is a cross-sectional view taken along lines A-A of FIG. 3 of an exemplary embodiment of a system 1000 in a second operative position.

Referring to FIG. 5, upon movement of actuation bar 1300 closer to handheld portion 1800, sheath seat 1330 can come in contact with sheath tip 6400, thereby causing sheath 6300 to buckle and/or crumble. As actuator bar 1300 comes in contact with handheld portion 1800, bar stop 1320 can approach medicament carrier stop 9400, while carrier spring 1600 is compressed.

Figure 6:
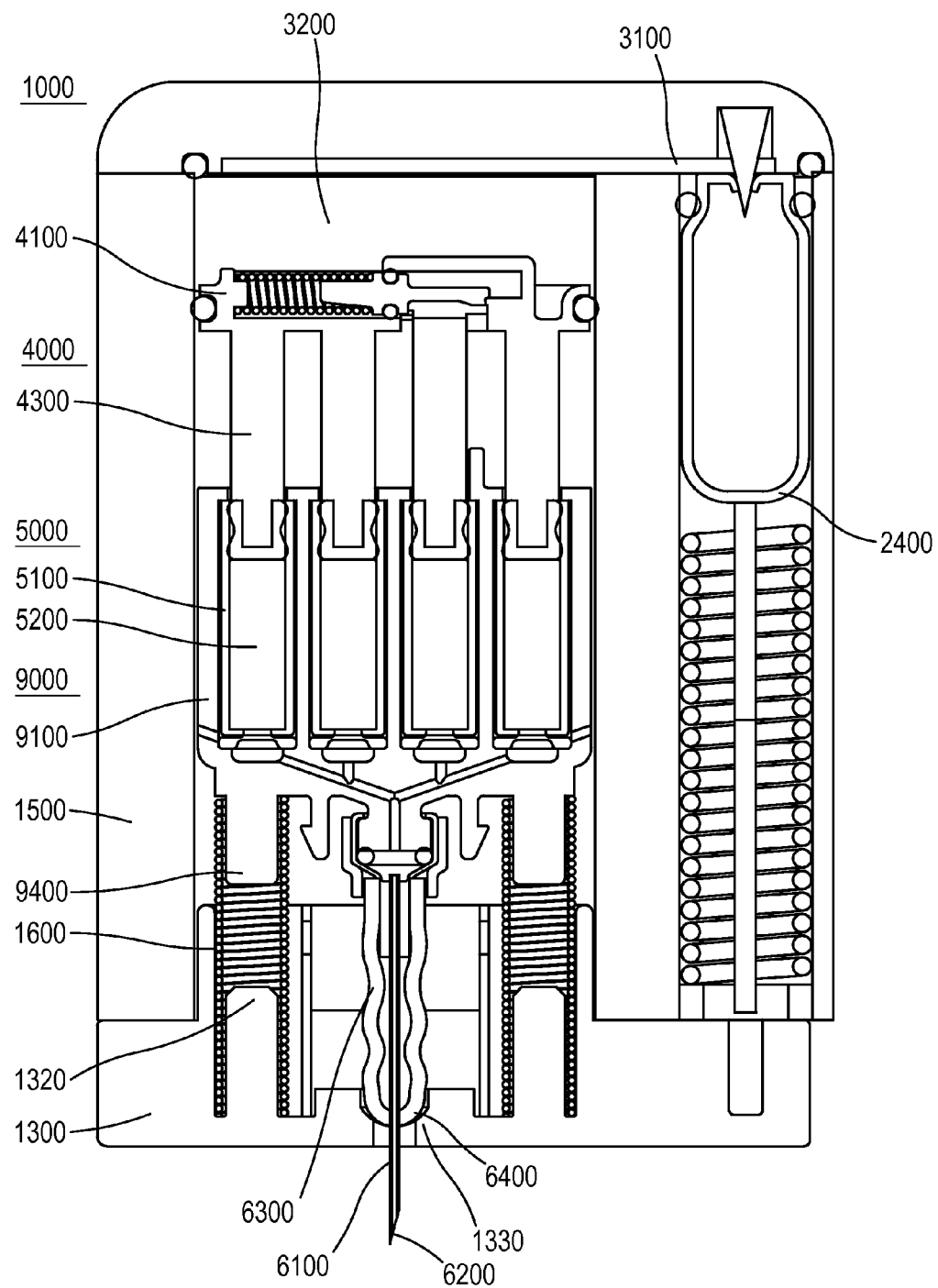
FIG. 6 is a cross-sectional view taken along lines A-A of FIG. 3 of an exemplary embodiment of a system 1000 in a third operative position.

Referring to FIG. 6, as at least a portion of contents 2500 of gas container 2400 escapes, it can flow through channel 3100. The gas, which can still be relatively pressurized, can begin to accumulate behind pusher 4100 to form an expanding gas chamber 3200 and to cause medicament actuator 4000, medicament storage assembly 5000, and medicament carrier 9000 to slide together within sleeve 1500. As medicament actuator 4000, medicament storage assembly 5000, and medicament carrier 9000 slide closer to actuator bar 1300, spring 1600 becomes increasingly compressed between bar stop 1320 and medicament carrier stop 9400. As medicament actuator 4000, medicament storage assembly 5000, and medicament carrier 9000 slide closer to actuator bar 1300, needle tip 6200 can extend further from actuator bar 1300 and sheath 6300 can become further compressed and/or deformed. At its ultimate extension point, needle tip 6200 can extend from housing 1100 from approximately 0.25 millimeters to approximately 20 millimeters, including all values and subranges therebetween, such as up to approximately 2 millimeters, greater than approximately 5 millimeters, from approximately 5.13 millimeters to approximately 9.98 millimeters, etc.

Figure 7:
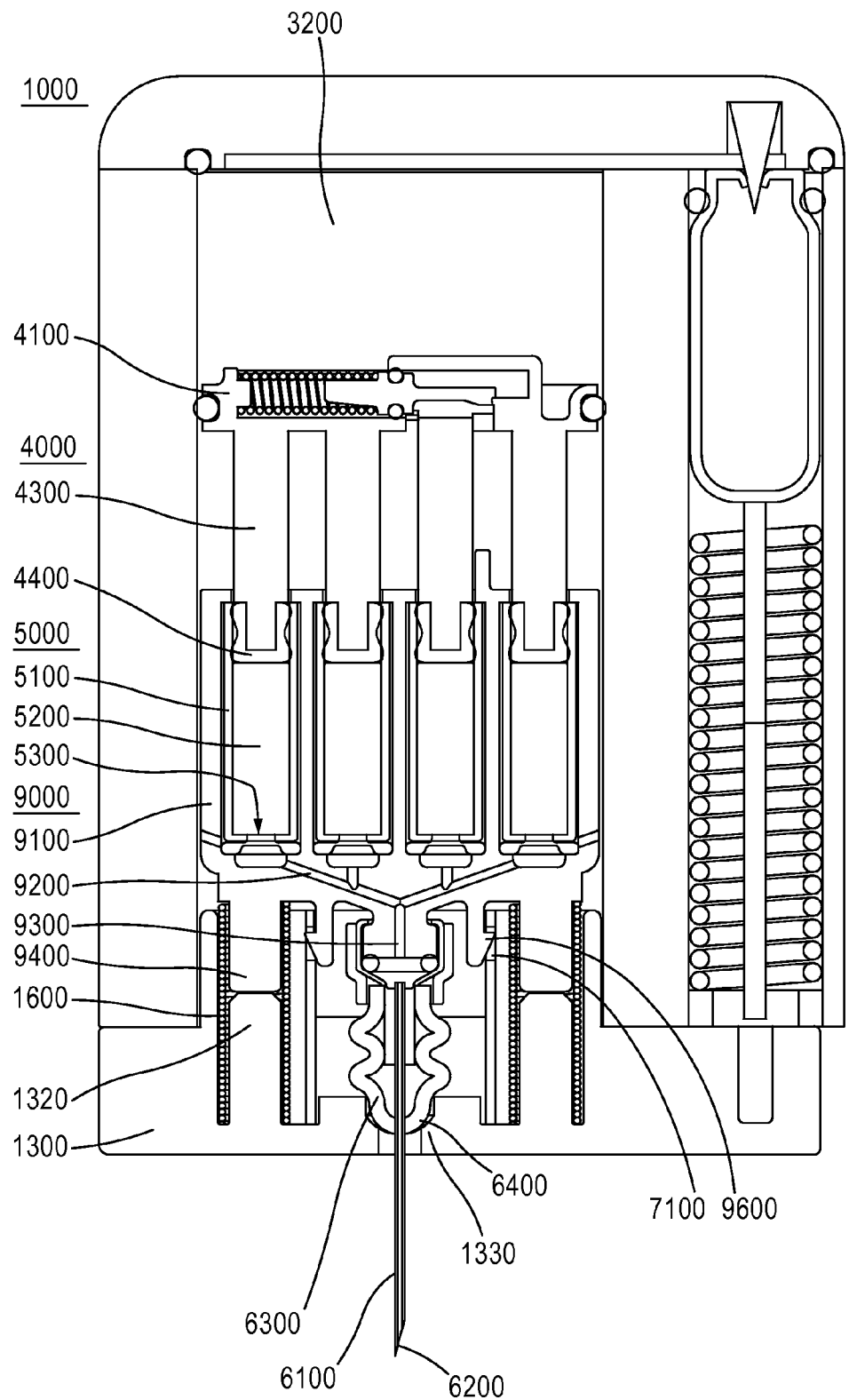
FIG. 7 is a cross-sectional view taken along lines A-A of FIG. 3 of an exemplary embodiment of a system 1000 in a fourth operative position.

Referring to FIG. 7, as gas chamber 3200 continues to expand, medicament carrier 9000 can be driven until medicament carrier stop 9400 contacts actuator bar stop 1300 thereby resisting further travel of medicament carrier 9000. At that point, additional expansion of gas chamber 3200 can cause medicament actuator 4000, pusher bar 4100, plungers 4300, and/or pistons 4400 to initiate travel with respect to medicament storage assembly 5000, thereby generating an expulsion pressure in vials 5100, and/or thereby rupturing frangibles 5300 and allowing medicament 5200 to enter medicament carrier 9000, and begin flowing through medicament channels 9200, medicament conduit 9300, needle 6100, and/or out needle tip 6200 and into a patient. Alternatively, frangibles 5300 can be replaced and/or augmented by a frangible located at or near where medicament conduit 9300 couples to needle 6100. Frangibles 5300 can be constructed of a thin, taught, resilient, durable, and/or sealing material potentially having a predetermined yield strength, such as a rubber, such as chromo butyl rubber, and/or of a relatively brittle material potentially having a predetermined yield strength, such as ceramic, certain plastics, such as polystyrene, etc.

As medicament carrier stop 9400 contacts actuator bar stop 1300, medicament carrier hooks 9600 can engage with engagement receivers 7100 in use indicator 7000.

Figure 8:
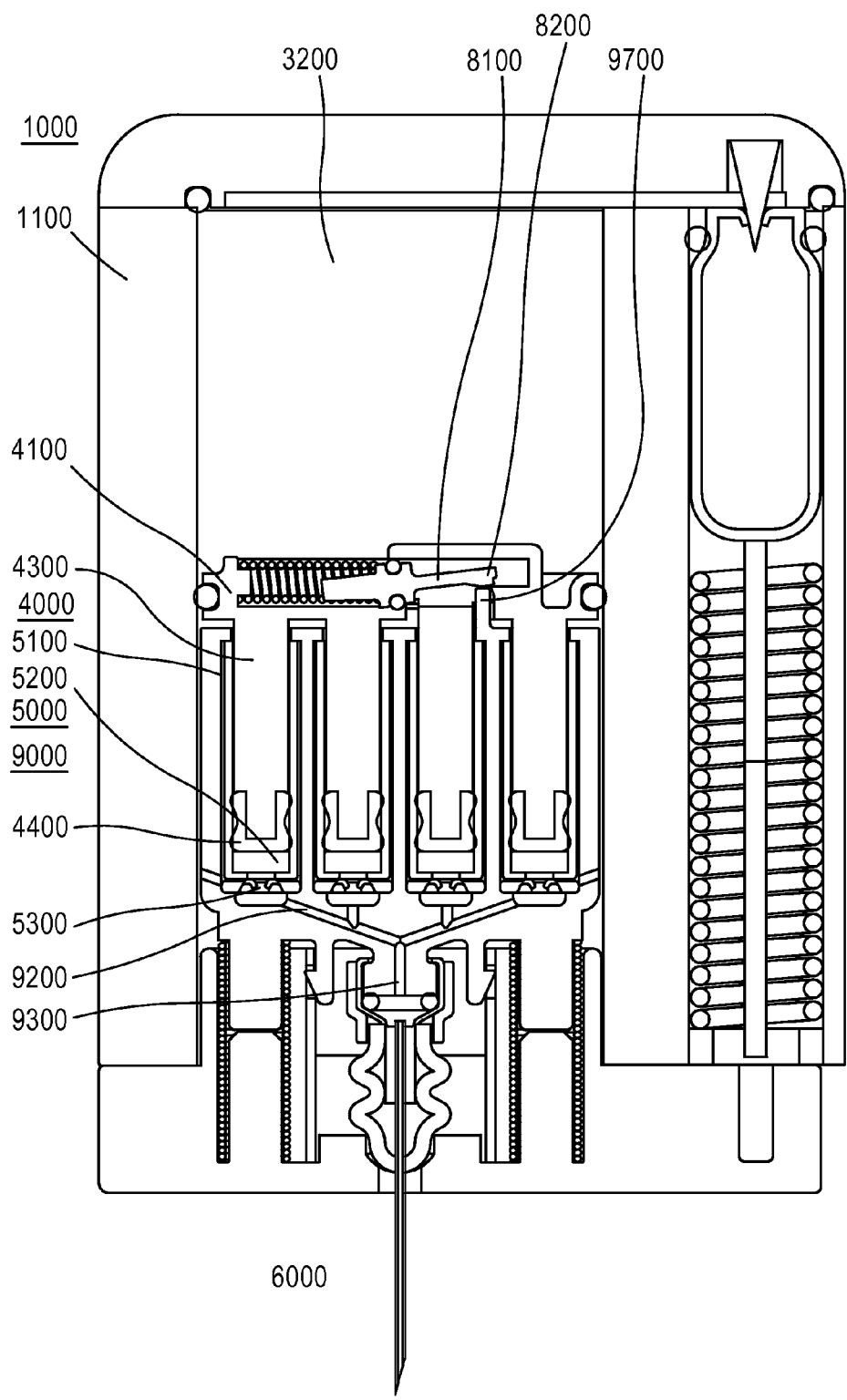
FIG. 8 is a cross-sectional view taken along lines A-A of FIG. 3 of an exemplary embodiment of a system 1000 in a fifth operative position.

Referring to FIG. 8, as gas chamber 3200 continues to expand, medicament actuator 4000, pusher bar 4100, plungers 4300, and/or pistons 4400 can continue moving until they complete their travel within medicament storage assembly 5000, thereby expelling a predetermined dose of medicament 5200 from vials 5100, out of needle assembly 6000, external to housing 1100, and/or into the patient. As gas chamber 3200 reaches its maximum size, medicament actuator 4000, pusher bar 4100, plungers 4300, and/or pistons 4400 can continue moving until they complete their travel with respect to medicament carrier 9000, thereby causing gas release actuator 9700 to engage with gas release valve 8200. Engagement of gas release actuator 9700 with gas release valve 8200 can cause within gas chamber 3200 to exit gas chamber 3200, discharge away from pistons 4400, and/or exhaust from system 1000 and/or housing 1100, such as via status indicator 1400 and/or a gas escape port located on housing 1100).

Figure 9:
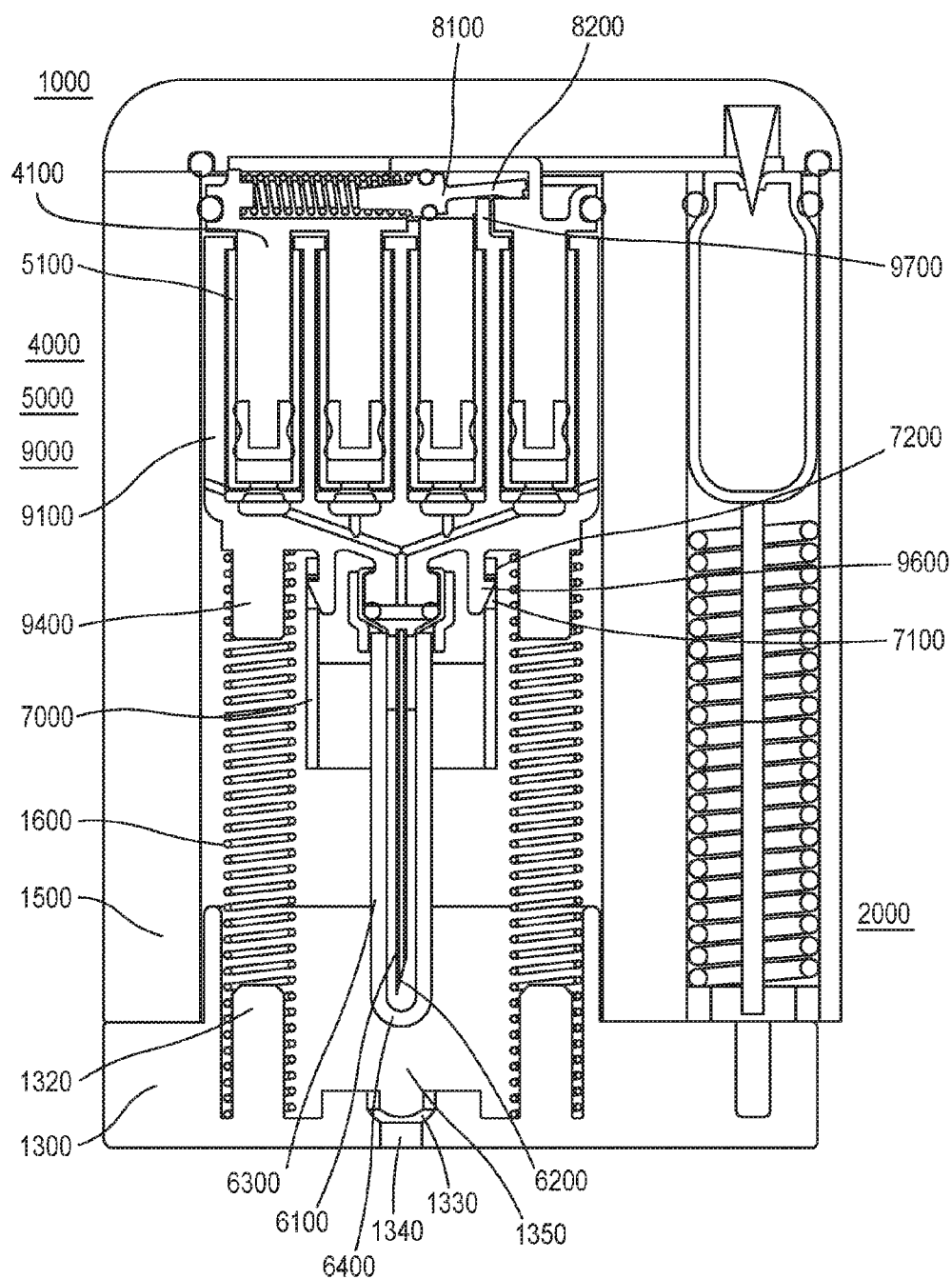
FIG. 9 is a cross-sectional view taken along lines A-A of FIG. 3 of an exemplary embodiment of a system 1000 in a sixth operative position.

Referring to FIG. 8 and FIG. 9, as sufficient gas is vented from gas chamber 3200, the pressure applied by the gas in gas chamber 3200 can decrease until the force applied by the gas on medicament actuator 4000 is less than the force of compressed spring 1600. Thus, spring(s) 1600 can begin to expand, thereby moving medicament carrier 9000, vial assembly 5000, and medicament actuator 4000 away from actuator bar 1300 and helping to exhaust gas from gas chamber 3200. As medicament carrier 9000 moves, use indicator 7000 can travel with it, due to the engaged relationship of medicament carrier hooks 9600 and engagement receivers 7100 and/or engagement catches 7200 in use indicator 7000. As use indicator 7000 moves away from actuation bar 1300, sheath 6300 can travel with it, thereby creating a gap between sheath tip 6400 and needle port 1340, and thereby exposing a previously non-visible colored portion 1350 of actuation bar 1300 and/or providing an indication that system 1000 has been used (and likely substantially exhausted of its medicament), thereby discouraging any further attempts to use system 1000.

As medicament carrier 9000 moves away from actuator bar 1300, needle 6100 can retract into sheath 6300 which un-buckles and/or un-deforms towards its original shape. Eventually, needle 6100 can retract completely within the boundaries of housing 1100, thereby tending to prevent accidental needle sticks after the initial injection and/or potentially reducing and/or eliminating a sharps hazard.

In certain exemplary embodiments, system actuator 2000 can comprise a finger triggered, twistable, pivotable, and/or lever-operated mechanism. For example, system actuator 2000 can comprise a twistable handle that can screw into gas port 2600. In certain exemplary embodiments, system actuator 2000 can be a finger trigger located on a side of the housing.

Figure 10:
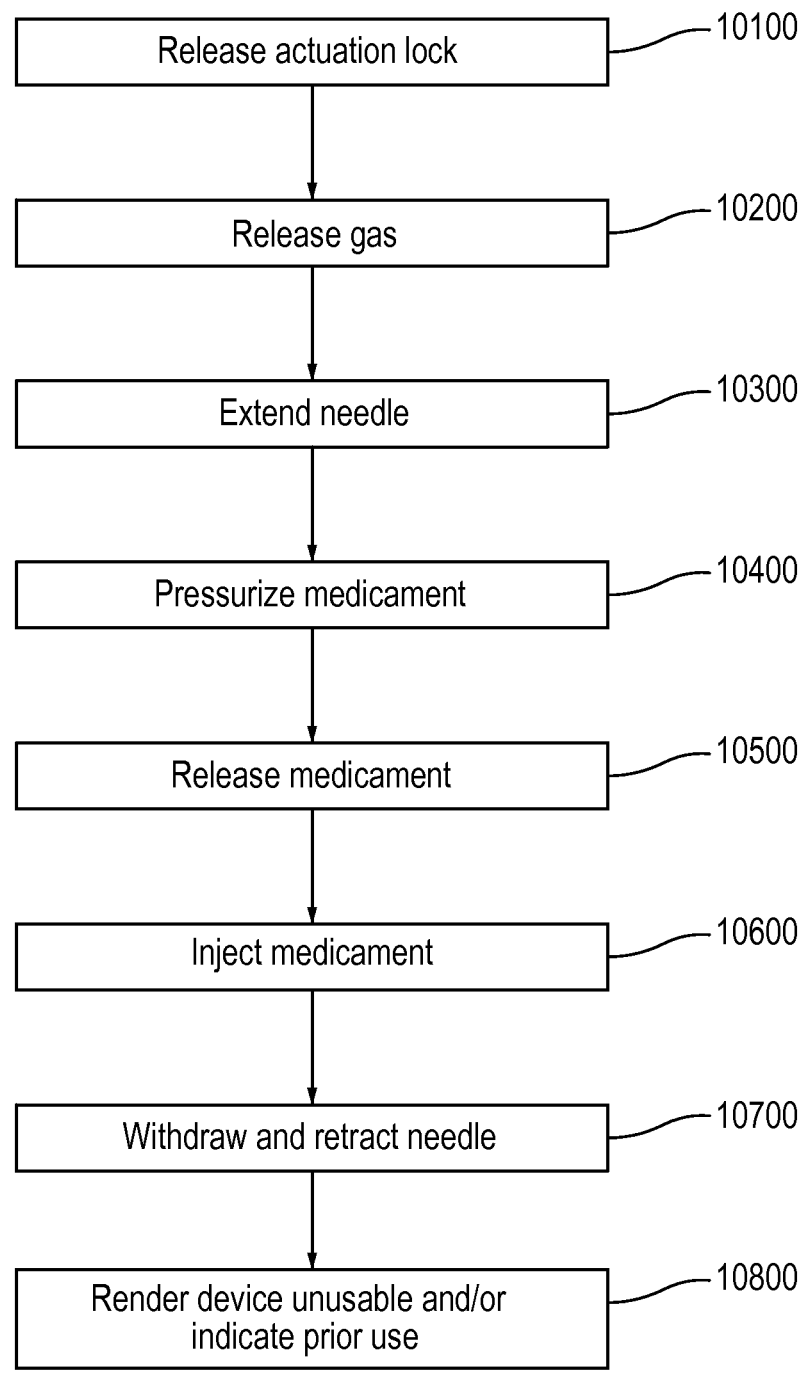
FIG. 10 is a flowchart of an exemplary embodiment of a method 10000.

FIG. 10 is a flowchart of an exemplary embodiment of a method 10000 for operating a medicament delivery apparatus. At activity 10100, an actuation lock for the apparatus is released. At activity 10200, an actuating portion of the contents of a compressed gas container are released. At activity 10300, via pressure provided by the released gas, a needle is extended from the apparatus. At activity 10400, via pressure provided by the released gas, a piston applies pressure to a medicament stored in one of a plurality of vials.

At activity 10500, a frangible containing the medicament in the vial is burst. At activity 10600, the medicament flows from the vial, through the needle, and into a patient. At activity 10700, once a predetermined dose is expelled and/or injected, the needle is withdrawn from the patient and/or retracted into the pre-use bounds of the apparatus. At activity 10800, the apparatus is rendered unusable for additional injections and/or indicated as previously utilized.

Figure 11:
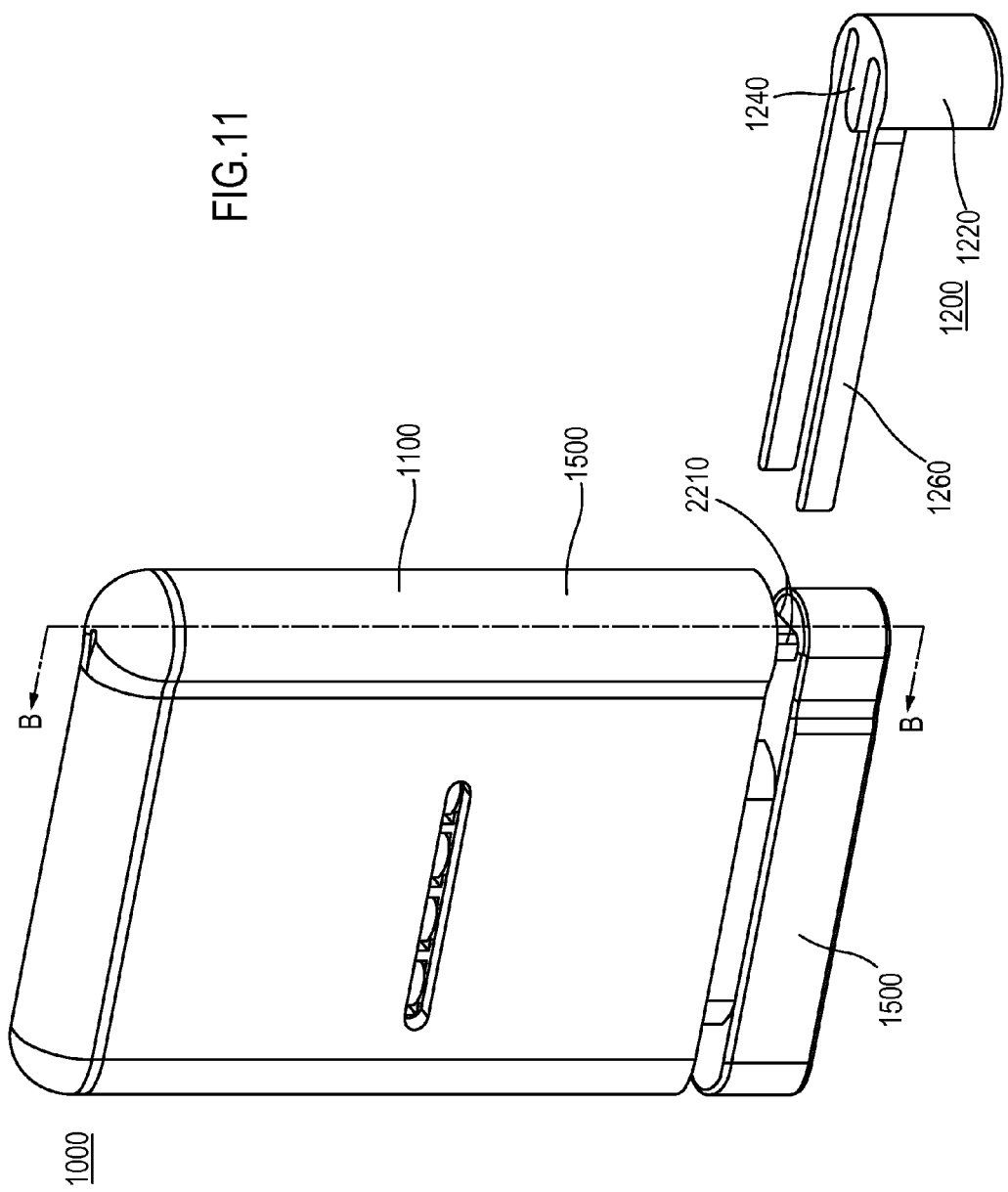
FIG. 11 is a perspective view of an exemplary embodiment of system 1000.

FIG. 11 is a perspective view of an exemplary embodiment of system 1000, showing actuation guard 1200 removed from housing 1100, so that actuation guard 1200 no longer separates actuator bar 1300 from handheld portion 1800. Actuation guard 1200 can comprise a grippable portion 1220 that can be gripped by a user to pull actuation guard 1200 away from housing 1100, thereby allowing system 1000 to be activated, such as via slapping actuator bar 1300 against a thigh of the user. Actuation guard 1200 can comprise an actuation stick separator portion 1240, that can keep separate actuation stick prongs 2240 when actuation guard 1200 is installed on housing 1100. Actuation guard 1200 can comprise a guard portion 1260 that can separate actuator bar 1300 from handheld portion 1800 when system 1000 is not in use and/or when system 1000 has not been used.

Figure 12:
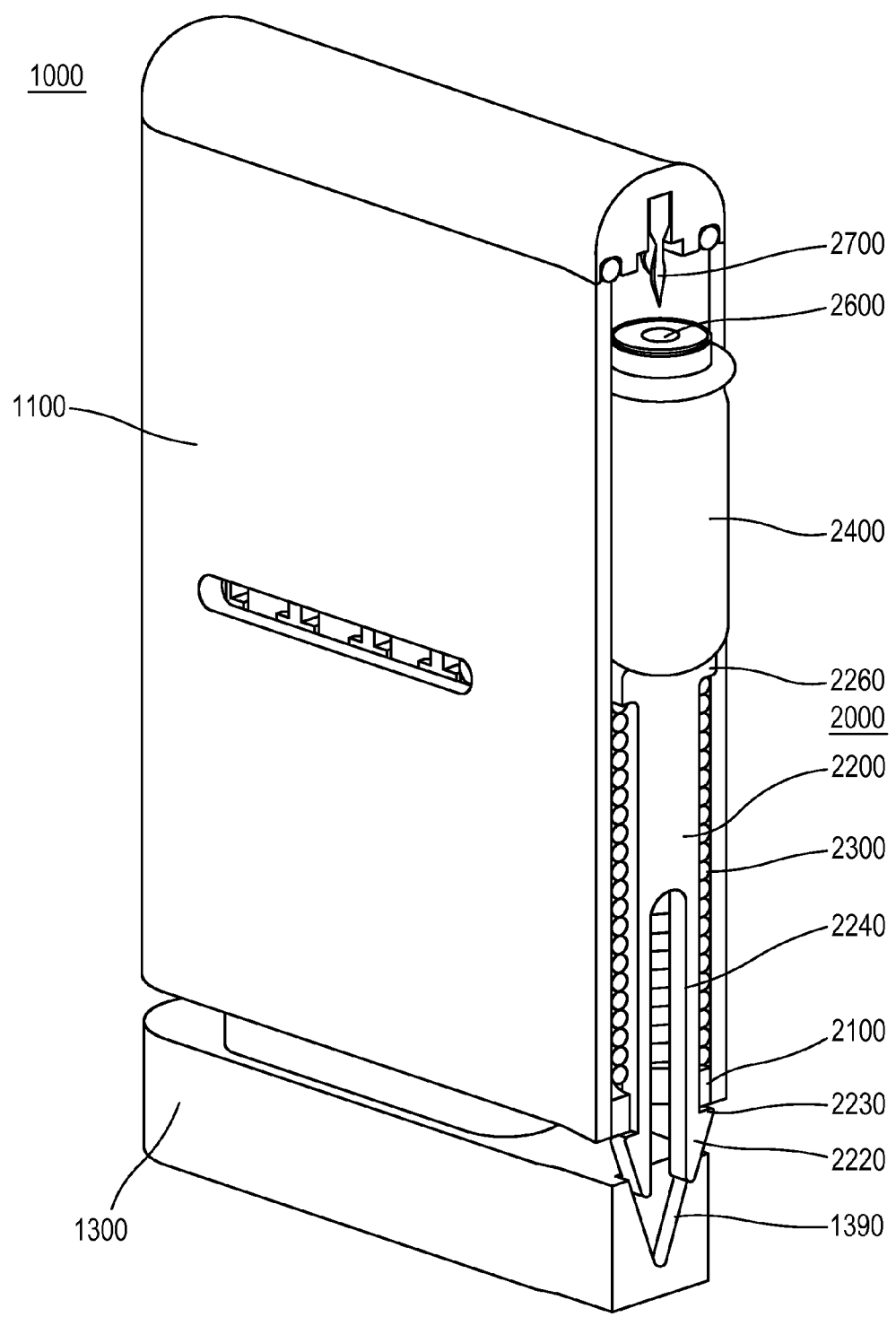
FIG. 12 is a perspective cross-sectional view taken along lines B-B of FIG. 11.
Figure 13:
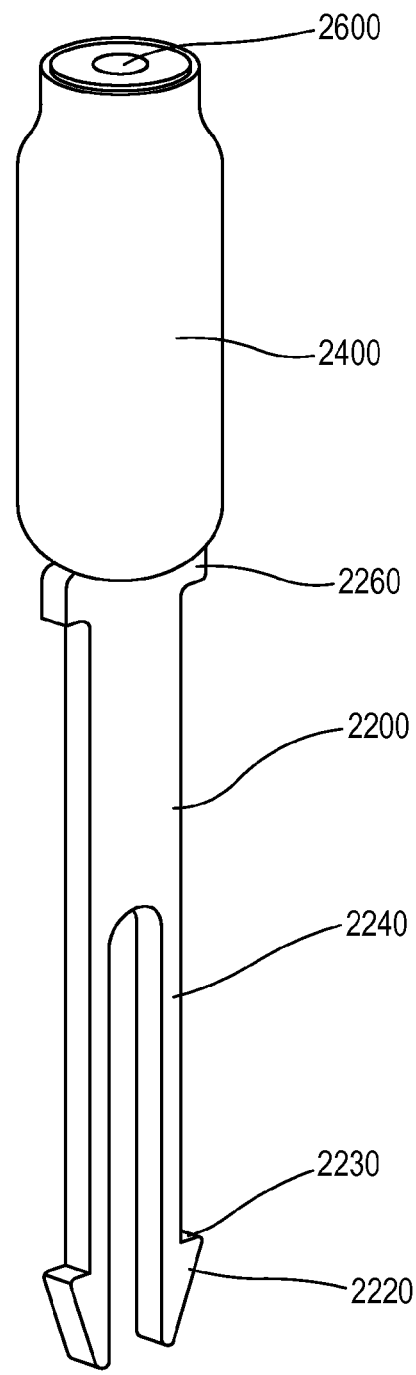
FIG. 13 is a perspective view of an exemplary embodiment of actuation stick 2200.

FIG. 12 is a perspective cross-sectional view taken along lines B-B of FIG. 11, and FIG. 13 is a perspective view of an exemplary embodiment of actuation stick 2200. Referring to FIGS. 12 and 13, system 1000 can comprise housing 1100, actuation bar 1300, and system actuator 2000, which can comprise prong squeezer 1390, actuation stick 2200, prong retainer 2100, spring 2300, upper spring retainer 2260, gas container 2400, gas port 2600, and/or puncturer 2700. When actuation bar 1300 is pressed firmly against a user's body, such as via slapping housing actuation bar against the user's thigh, buttocks, and/or arm, prong squeezer 1390 can urge prong tips 2220 of prongs 2240 of actuation stick 2200 toward one another. Note that prong tips 2200 can have a triangular, wedge, angular, and/or frustro-conical shape. As prongs tips 2220 slide along the angled V-groove of prong squeezer 1390, prong catches 2230 can substantially loose contact with prong retainer 2100. This can allow compressed spring 2300 to rapidly urge actuation stick 2200 and gas container 2400 toward puncturer 2700, which can penetrate gas port 2600, thereby allowing gas to escape from gas container 2400. Although any of many different types of gas containers can be utilized, an exemplary gas container can be obtained from Leland Limited, Inc. of South Plainfield, N.J.

Figure 14:
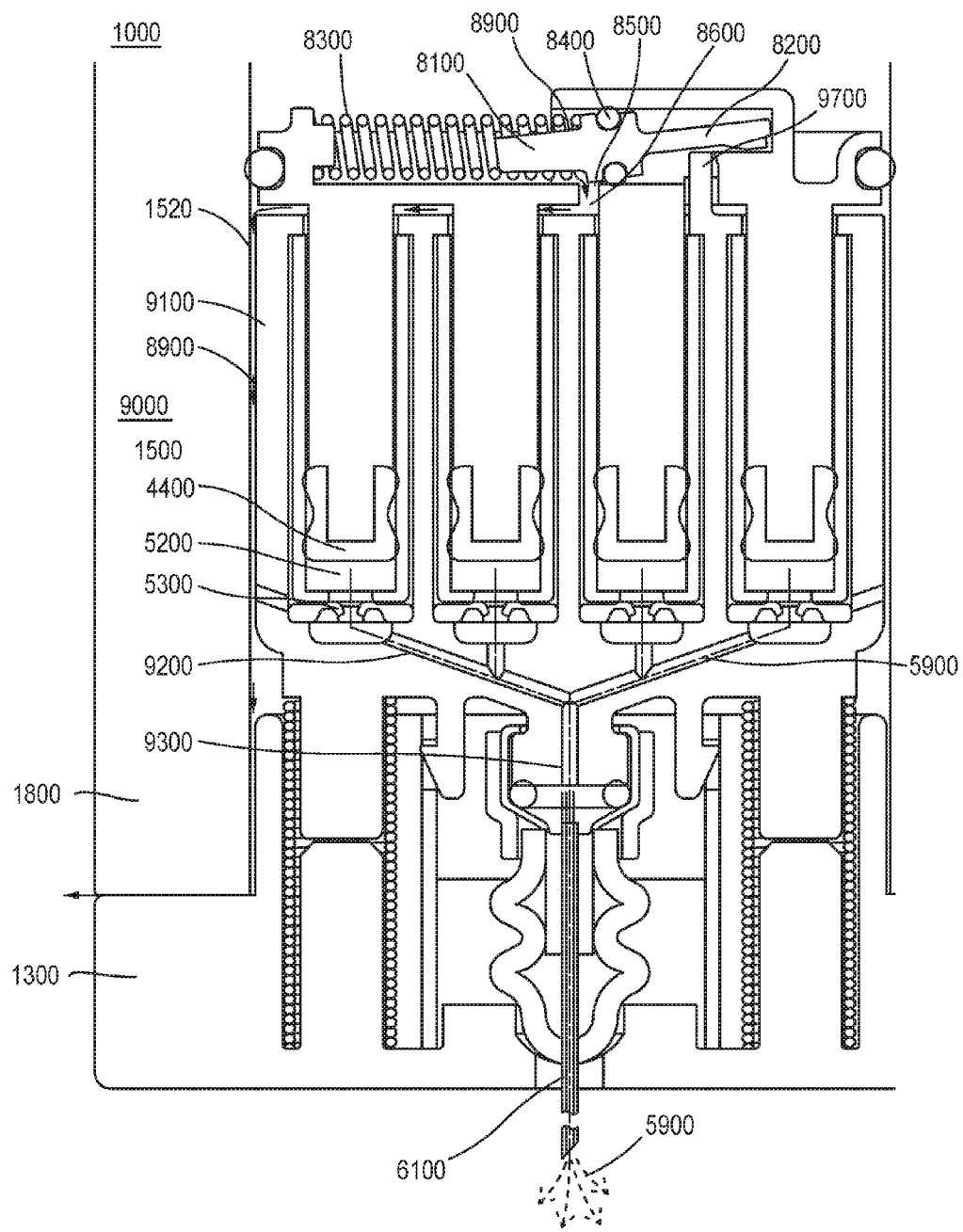
FIG. 14 is a cross-sectional view of an exemplary embodiment of gas venting mechanism 8000 taken along lines A-A of FIG. 3.

FIG. 14 is a cross-sectional view of an exemplary embodiment of gas venting mechanism 8000 of system 1000 taken along lines A-A of FIG. 3. System 1000 can comprise handheld portion 1800, actuator bar 1300, sleeve 1500. As pistons 4440 near the limit of their travels, medicament 5200 can be expelled along medicament path 5900, which can extend past frangible 5300, through medicament channels 9200, medicament conduit 9300, and needle 6100, and into the body of a user, such as subcutaneously, intramuscularly, and/or at a depth of from approximately 0.25 millimeters to approximately 20 millimeters, including all values and subranges therebetween, such as up to 2 millimeters, greater than 5 millimeters, etc.

As pistons 4440 near the limit of their travels, engagement of gas release actuator 9700 with gas release valve 8200 can cause compressed spring 8300 to move valve arm such that o-ring 8400 is urged away from its seat 8500. This movement can reveal a passage 8600, via which gas can exit gas chamber 3200 along gas exhaust path 8900, which can extend between sleeve inner walls 1520 and outer walls 9100 of medicament carrier 9000. Eventually, gas exhaust path 8900 can extend between handheld portion 1800 and actuator bar 1300. Likewise, an alternative embodiment of valve 8200, made of rubber or any other resilient material, can be placed across seat 8500 to provide a seal that, once gas release actuator 9700 interacts with valve 8200, allows valve 8200 to bend or flap upwards away from seat 8500, causing the gas to escape via passage 8600.

The following paragraphs expands on the above and describe various exemplary embodiments relating to compact auto-injectors that can comprise and/or utilize a vial or a plurality of vials to store and/or contain an injectable medicament. These auto-injectors can have a compact form factor, such as approximately the size of a credit card. There are many methods of delivering such medicaments in such compact devices. The below descriptions cover multiple methods and/or mechanisms that can effectively administer a medicament using a compact auto-injector.

Exemplary Embodiment One: Methods of Utilizing an Auto-Injector

This exemplary embodiment describes a method of implementing an auto-injector utilizing a spring and/or gas driven system to administer a medicament and/or comprises a needle protection system.

An embodiment for delivering medicament from a chamber can comprise a vial or plurality of vials; said chamber in communication with a needle that can be concealed initially by some shield and/or sheath; extending said needle from the sheath at least 1 mm and/or inserting the needle past a needle insertion point to an injection site at a depth of at least 5 mm; the application of a force that can originate from the contents of a gas cylinder and/or by means of a spring or multiple springs sufficient to eject medicament held within said chamber into the needle and/or through the needle insertion point to a depth of at least 5 mm to deliver up to 5 ml of medicament into the injection site in less than 5 seconds; wherein the medicament can be injected and/or held through the use of a vial system that comprises a plunger, vial(s), reservoir, and/or needle that can be located within said chamber; wherein the force can be applied on the plunger at the proximal end allowing for the plunger, vial(s), reservoir, and/or needle to travel towards the distal end of the housing; wherein the plunger can slideably travel through the vial towards the distal end to allow for the appropriate dose of medicament to be delivered; wherein the needle insertion point can be located more superficial than the injection site; wherein the needle can have a length of at least 6 mm and/or the medicament can be ejected at a pressure of at least 25 p.s.i. at a rate of at least 0.20 ml/sec; and/or wherein the needle can retract into the shield and/or housing and/or a needle protection portion slides over the needle following delivery of the medicament.

Figure 15:
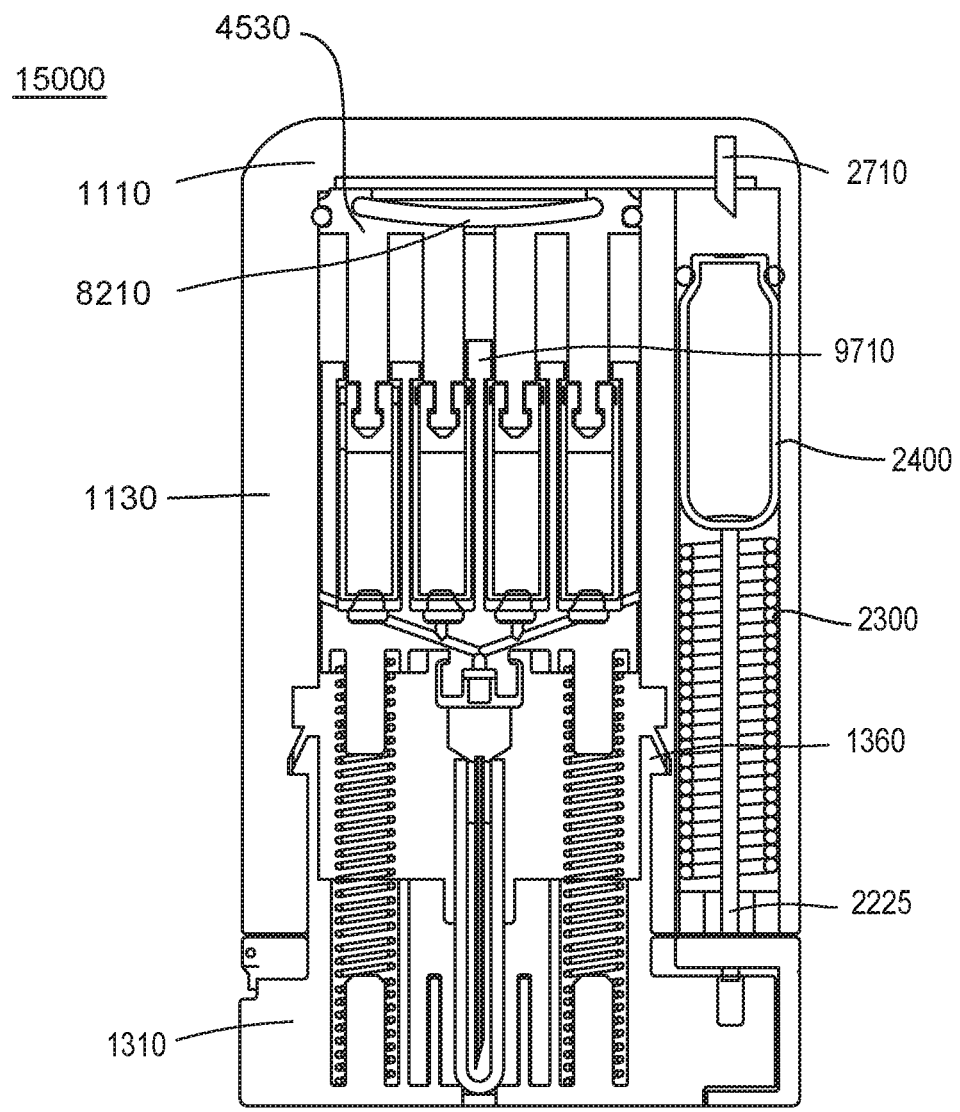
FIG. 15 is a cross-sectional view taken along lines A-A of FIG. 3 of an exemplary embodiment of a system 15000.

FIG. 15 shows an exemplary embodiment an auto-injector 15000. Though the figure shows the force mechanism used as being a compressed gas container 2400, the force method can be created by a spring force (See description of FIGS. 18A and 18B below). The top of the housing 1110 can be laser-welded to ensure stability due to high pressure. Likewise, the entire housing 1130 can be a sealed housing, and may be made smaller by eliminating screws and/or pins holding the base 1310 and/or top 1110 to the housing. In FIG. 15, this can be completed by adding hooks 1360 to the base 1310. The hooks 1360 can allow the base 1310 to slide into the housing 1130, thus pushing the detents 2225 inward and allowing for the puncturing of the gas cylinder 2400 by activating the compressed spring 2300. These hooks 1360 can also click into the housing 1130, making the base 1310 unable to move post-injection; this eliminates re-use of the device and acts as an indicator to determine if the device has been used or if the device has not been activated. The gas release mechanism is also a novel addition to the device. A rubber flap 8210 (also referred to as a gas release flap) and/or other resilient material can be located inside the plunger bar 4350. A solid piece 9710 or member can stick up from the reservoir near the top of the vials. Once the plunger bar 4350 dispenses the medicament, this piece 9710 can push the rubber flap up, thereby releasing excess gas in the system. The puncturing device for the gas cylinder could be a roll-pin 2710 that is sliced at a 45 degree angle to ensure sharpness for puncturing.

FIG. 16 shows the safety tab 1210 used to protect the user from accidental activation. FIG. 16 also shows an extended portion 1215 of the safety tab 1210 with grooves 1218 added to it. This can aid the user in removing the safety tab 1210 by creating a larger gripping surface and/or a more tactile feel to the tab.

Exemplary Embodiment Two: Chemical Reaction

This exemplary embodiment involves an auto-injection system that utilizes a chemical reaction as an activation mechanism to deliver the medicament into a patient. It also comprises a needle protection system.

This exemplary embodiment comprises a delivery system that can encompass a housing, vial or plurality of vials, plunger for each vial, single needle or needle cannula, and medicament or medicaments within the vial or plurality of vials; the vial or plurality of vials in communication with the plunger(s) at proximal end and in communication with a reservoir that contains a single needle or needle cannula at the distal end; the needle can be protected by some sheath/shield; a chemical reaction capable of occurring when one chemical is allowed to interact with another chemical and/or a substance that may create such a reaction through the use of some activation mechanism; and said chemical reaction that can generate a force that is strong enough to drive said plunger, vial, reservoir, and needle towards the distal end of the housing; the needle exiting said sheath/shield and entering an injection site; the plunger(s) slideable in the vial(s) that contain the medicament; and said medicament exiting the vials into through the reservoir and needle cannula into the injection site; upon exit of the desired contents of the vial, the entire needle, reservoir, vial, and plunger assembly can retract towards the proximal end of housing by some means such as a wire, spring, o-ring, and/or rubber membrane and/or a needle protection portion slides over the needle following delivery of the medicament.

Figure 17:
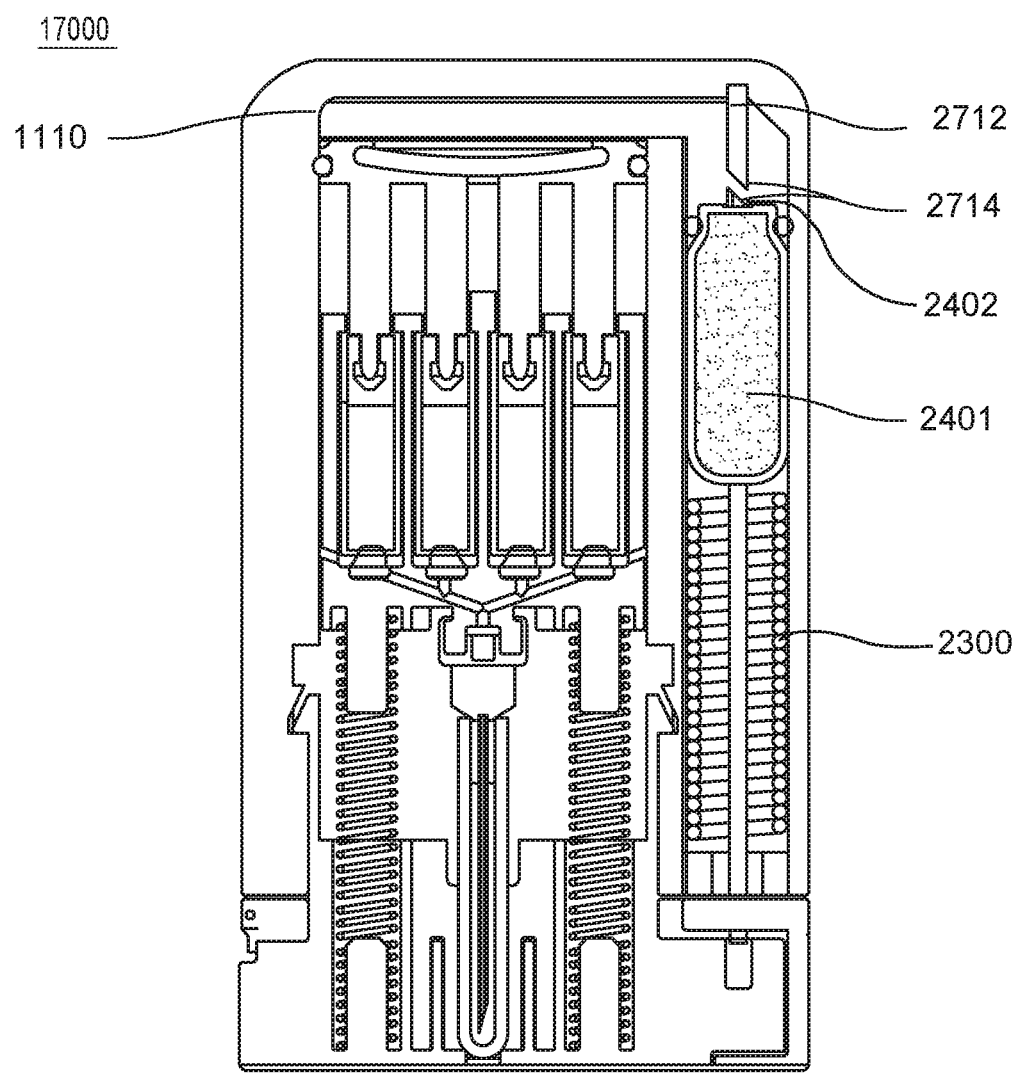
FIG. 17 is a cross-sectional view taken along lines A-A of FIG. 3 of an exemplary embodiment of a system 17000.

FIG. 17 is a view of the compact injector 17000 with several modifications to allow for a chemical reaction to occur as the primary force method in order to deliver the medication. In the particular drawing, the puncturing pin 2712 can include a rough surface 2714. Likewise, the container 2401 used in the device can have a similar rough material and/or surface 2402, and can contain mostly Sodium Azide (NaN3). Once the spring 2300 (attached to the container) is activated, the two rough surfaces 2714, 2402 can simultaneously come in contact with each other to create a spark and puncture the Azide container. This can create an immediate chemical reaction because of the spark. The reaction (2 NaN3→2 Na+3 N2) can form hot nitrogen gas and sodium in order to create enough force to inject the medication. A modification to this figure can be made to include another container at the top in place of the puncturing pin that can break open from the force of the spring and second container, thus mixing the two chemicals and can cause a chemical reaction to occur in order to produce the force needed.

Exemplary Embodiment Three: The Spring Driven Injector

Certain exemplary embodiments of the auto-injector can use a spring or multiple springs to inject the medicament into a patient. The novelty of this system can lie in the orientation of the activation springs and the vial system (that comprises the plunger, vial(s), reservoir and the needle/cannula) system. Because the activation springs can be located in parallel to the vial system, the device can be smaller than existing devices on the market (that are linear in nature), potentially having a form factor that is approximately the size of a credit card.

Certain exemplary embodiments can comprise a delivery system that can encompass a housing, vial or plurality of vials, plunger for each vial, single needle or needle cannula, and medicament and/or medicaments within the vial or plurality of vials; the vial or plurality of vials in communication with the plunger(s) at proximal end and in communication with a reservoir that contains a single needle or needle cannula at the distal end; the needle protected by some sheath/shield; the housing further comprising at least one spring (this can comprise a gas spring, coil spring, leaf spring, etc.) wherein the spring(s) is parallel to the plunger, vial(s), and reservoir system and is in communication with a solid member (that can be made of rubber, plastic, metal, and/or some other resilient material) that is also in communication with the proximal end of the plunger such that when the spring(s) is activated, a force is applied on the plunger at the proximal end allowing for the plunger(s), vial(s), reservoir, and needle to travel towards the distal end of the housing; wherein the plunger can slideably travel through the vial towards the distal end to allow for the appropriate dose of medicament to be delivered; the solid member is displaced away from the plunger, which can allow for the retraction of the entire needle, reservoir, vial(s), and plunger assembly towards proximal end of housing by some means such as a wire, spring, o-ring, and/or rubber membrane and/or for a needle protection portion to slide over the needle following delivery of the medicament.

Figure 18A:
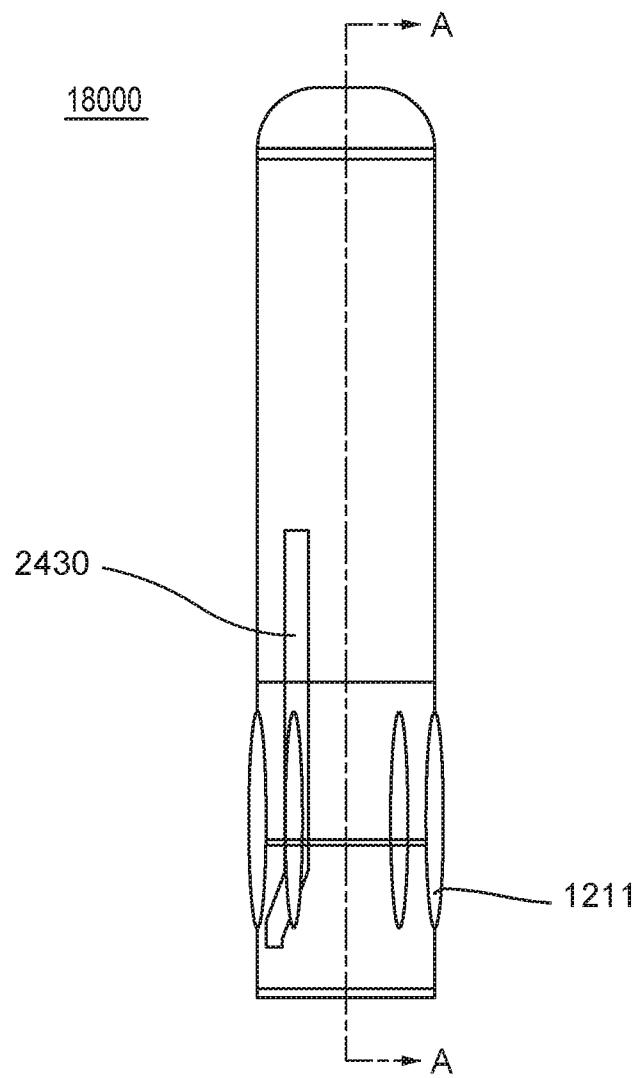
FIG. 18A is an end view of an exemplary embodiment of a system 18000.
Figure 18B:
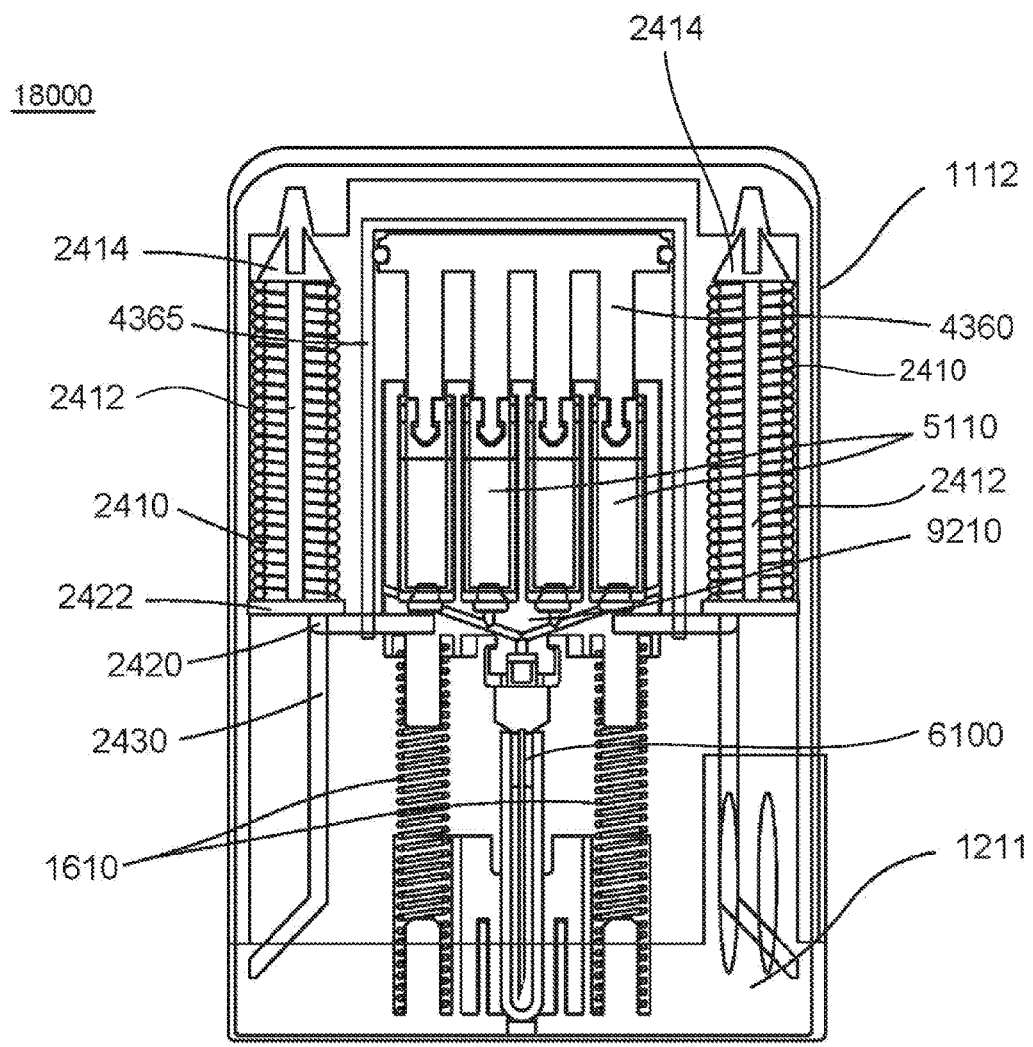
FIG. 18B is a cross-sectional view taken along lines A-A of FIG. 18A of an exemplary embodiment of a system 18000.

FIGS. 18A and 18B shows several views of the spring driven injector 18000. The primary force used to push down the pusher bar 4360, vial system 5110, reservoir 9210, and needle 6100 can be provided by compressed springs 2410. In the cross-section drawing (FIG. 18B), two springs 2410 can be located on the outside of the central chamber (containing the pusher bar 4360, vials 5110, reservoir 9210, and needle 6100). The springs 2410 can be held in place by a rod 2412 coupled with hooks 2414. Each spring 2410 can have a rolling solid member 2420 attached to it that is also connected to a bar 2422 that is held into a notch/indentation in the reservoir 9210 near the bottom of the vials 5110. Furthermore, a solid beam 4365 can wrap around the top of the pusher bar 4360 and can attach to the aforementioned bar 2422. The bar 2422 can slide in and out of the reservoir 9210 and the solid beam 4365, but only if the rolling solid member 2420 is rolled away from the reservoir 9210 and beam 4365. The device can be activated by the user pulling out the safety mechanism 1211 and pushing downward on the outside sleeve 1112. This can cause the hooks 2414 from the rods holding the springs 2410 in place to pinch inward, thereby releasing the springs 2410 forcefully downward. As the springs 2410 are driven downward, the rolling solid member 2420 and bar 2422 can roll down through the solid member passage 2430, which detours out of and away from the reservoir 9210. As the rolling solid member 2420 is moved, the solid beam 4365 wrapped around the pusher bar 4360 can come down as well, pushing the needle 6100 into the user. The medication can then be delivered into the user and/or patient once the rolling solid member 2420 goes down even further, which can be continually driven by the force of the springs 2410. The solid member 2420 passage eventually can turn away from the vial system 5100 and reservoir 9210 (also shown in the side view drawing as a hidden line). This can slide the bar 2422 out of the reservoir 9210 and out of the beam 4365, allowing for the retracting springs 1610 to push the pusher bar 4360, vials 5100, reservoir 9210, and needle 6100 back into the housing.

Exemplary Embodiment Four: Pulley System

This exemplary embodiment can utilize a pulley system as the activation mechanism for injecting medicament into the patient and that can also comprise a needle protection system.

Certain exemplary embodiments can comprise a delivery system that can encompass a housing, vial or plurality of vials, plunger for each vial, single needle or needle cannula, and medicament or medicaments within the vial or plurality of vials; the vial or plurality of vials in communication with the plunger(s) at proximal end and in communication with a reservoir that can contain a single needle or needle cannula at the distal end; the needle that can be protected by some sheath/shield; the housing further comprising one or more spring pulley system(s) that can constitute a spring connected to some slideable resilient material such as a string, wire, wire coil, flat metallic band, etc. at the proximal end of the housing, and said material that can travel through a channel in the housing from the proximal end of the housing towards the distal end of the housing and then returning through a parallel channel towards the proximal end wherein this material is connected to a solid member (made of rubber, plastic, metal, and/or some other resilient material); the solid member in communication with the proximal end of the plunger such that when the spring is activated the spring can produce enough force to allow the pulley system to operate by having the resilient material, such as a cord, which can forcefully travel towards the proximal end of the housing and can cause the cord to move the solid member in communication with the plunger, vial(s), reservoir, and/or needle towards the distal end; wherein the needle can exit said sheath/shield and can enter an injection site; the plunger(s) slideable in the vial(s) that can contain the medicament; and said medicament can exit the vials into through the reservoir and/or needle cannula into the injection site; upon exit of the desired contents of the vial, the solid member can be displaced away from the plunger allowing for the entire needle, reservoir, vial(s), and/or plunger assembly to retract towards the proximal end of housing by some means such as a wire, spring, o-ring, and/or rubber membrane and/or a needle protection portion to slide over the needle following delivery of the medicament.

Figure 19:
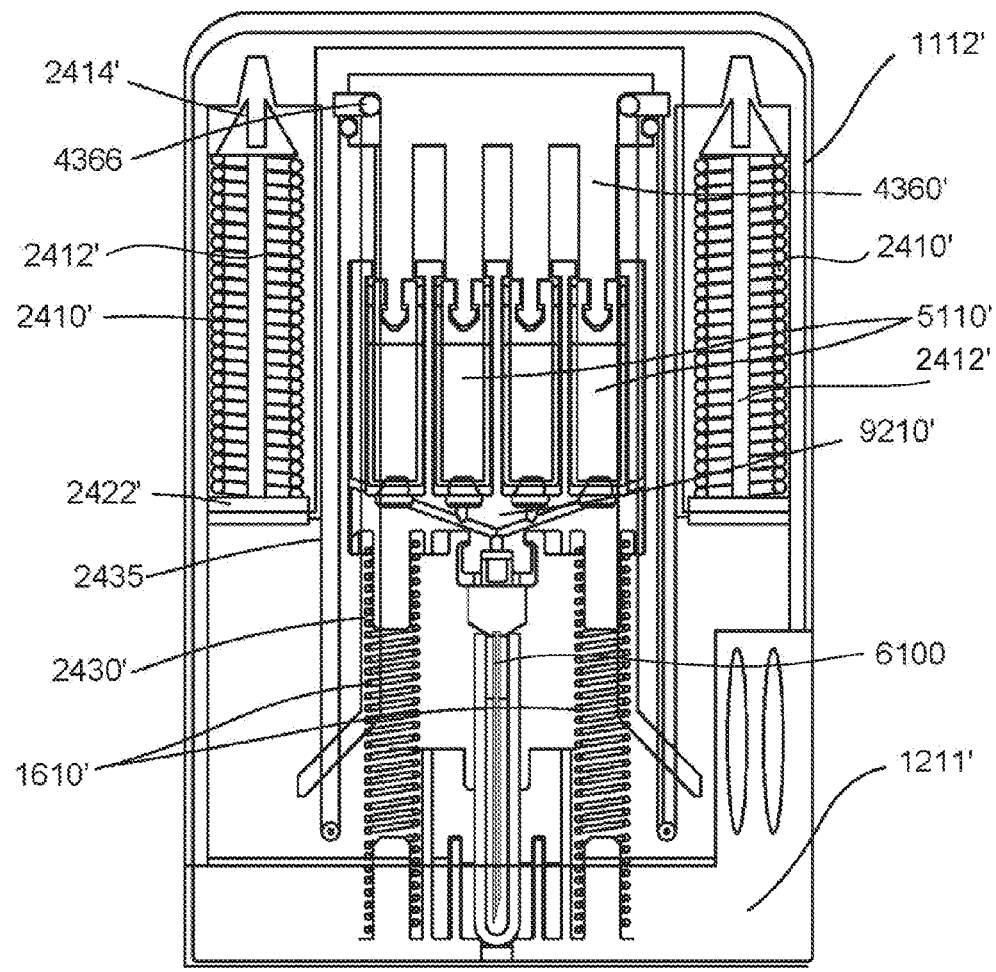
FIG. 19 is a cross-sectional view taken along lines A-A of FIG. 18A of an exemplary embodiment of a system 19000.

A pulley system 2435 is shown in the device 19000 depicted in FIG. 19 as the primary method for forcing the pusher bar 4360', vials 5110', reservoir 9210', and needle 6100 down for medicament injection. Similar to the above spring-driven injector 18000, the activation springs 2410' can be located parallel to the vial system 5110' and the device can be activated by the user pushing down on the outside sleeve 1112' of the device. The use of a pulley system 2435 can create a mechanical advantage, producing the proper force needed to efficiently push down the vial system 5100' and deliver the proper dose of medication. FIG. 19 shows a bar 2422' that can be connected to the end of the rod/spring member. This bar 2422' can be connected to the pulley system 2435 (that can comprise some resilient and/or moveable material). The other end of the pulley system 2435 can be connected on top of the pusher bar 4360' to a beam 4366 that can be able to slide when moved to a certain position. As the springs 2410' are driven downward, the pulley system 2435 can pull the pusher bar 4360', vials 5100' reservoir 9210' and needle 6100 down as well. Similar to the spring-driven injector, the solid beam member 4366 on top of the pusher bar 4360' can slide down the solid member passage 2430' and eventually dislodge from the pusher bar 4360'. Once this occurs, the entire system can retract back within the housing due to the force from the retracting springs 1610'.

Exemplary Embodiment Five: The Needleless Injector

This exemplary embodiment can comprise a Needleless Injector that can be gas and/or spring activated and that can allow for a user to inject a medicament into a patient without the use of a needle. The use of a plurality of vials can be considered the novel component and can allow the device to be compact in nature, such as having the approximate length and width similar to that of a credit card.

Certain exemplary embodiments for delivering medicament from a chamber can comprise a plurality of vials; the said chamber in communication with a passage into a small injection opening; the application of a force that can originate from the contents of a gas cylinder and/or by means of at least one spring that can eject medicament held within said chamber into the passage to the small injection opening, which can be defined and/or created by the housing and/or a small sterile rod that can be a needle or cannula allowing for the slight puncturing of the injection site in order to allow the medicament to be delivered, and through the tip of this small injection opening to a depth of at least 1 mm, that can deliver up to 5 ml of medicament into the injection site; wherein the medicament can be injected and held through the use of a vial system that comprises a plunger, vial(s), and/or reservoir all located within said chamber; wherein the force can be applied on the plunger at the proximal end allowing for the plunger, vial(s), and/or reservoir to travel towards the distal end of the housing; wherein the plunger can slideably travel through the vial towards the distal end to allow for the appropriate dose of medicament to be delivered through the reservoir into the small injection opening; wherein the injection opening point can be located more superficial than the injection site; wherein the medicament can be ejected at a pressure of at least 25 p.s.i. (For example, in such embodiments, the pressure to deliver a dose of 0.5 cc's could be about 100 pounds of force).

Figure 20:
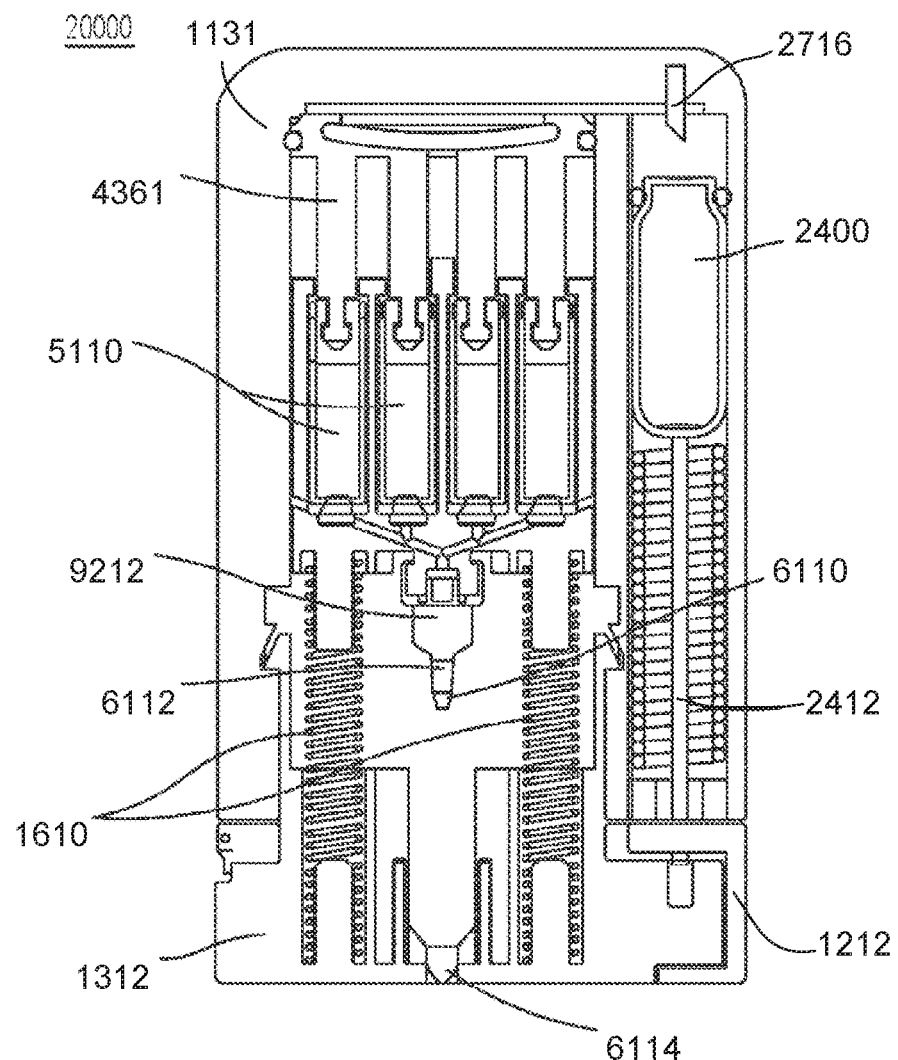
FIG. 20 is a cross-sectional view taken along lines A-A of FIG. 18A of an exemplary embodiment of a system 20000.

FIG. 20 depicts the components of the needleless injector 20000. The injector can be activated by removing a safety tab 1212 and pushing down on the housing 1131. The rod 2412 with hooks holding the spring 2410 in place can be initiated by the base 1312 moving upwards and pushing the hooks inward. The spring 2410 can drive the high pressure gas cylinder 2400 into a puncturing pin 2716, releasing the gas cylinder contents. The gas cylinder contents can push down the pusher bar 4361, vials and reservoir 9212 into the small opening 6114 at the base of the device near the injection site. The small opening 6114 allows passage of a medicament or agent and also a slight puncturing of the injection site. A tiny cannula 6110 and/or needle can be located at the bottom of the reservoir 9212 and/or can be used for slightly puncturing the injection site. The cannula defines a tiny orifice 6112 therein for passage of the medicament or agent. This slight puncture can allow the medicament stored in the vial 5100 to flow through the reservoir 9212 and into the injection site. Once the pressure is released, the entire system (including the pusher bar, vials, and reservoir) can be pushed back up within the housing by the retracting springs 1610.

Exemplary Embodiment Six: The Multi-Pharmaceutical Injector

This exemplary embodiment can comprise a compact auto-injector that can incorporate a plurality of vials, allowing for multiple medicaments to be injected at one time or at different times. The use of a plurality of vials can be considered the novel component and also can have the advantage of creating a device that is compact in nature, such as one having the length and width of a credit card. The device also can comprise a needle protection system.

Certain exemplary embodiments for delivering medicament from a chamber can comprise a plurality of vials; the said chamber or chambers in communication with a needle or needles that can be concealed initially by shields and/or sheaths; that can extend said needle from the said sheath at least 1 mm and can insert the needle past a needle insertion point to an injection site at a depth of at least 5 mm; the application of a force and/or forces that can originate from the contents of a gas cylinder and/or multiple gas cylinders, and/or by means of a spring and/or springs sufficient to eject medicament held within said chamber into the needle and through the needle insertion point; wherein the medicament can be injected and held through the use of a vial system and/or vial systems that can comprise a plunger, vial, reservoir, and/or needle all located within said chamber(s); wherein the force can be applied on the plunger at the proximal end allowing for the plunger, vial, reservoir, and/or needle to travel towards the distal end of the housing; wherein the plunger can slideably travel through the vial towards the distal end to allow for the appropriate dose of medicament to be delivered; wherein the needle insertion point can be located more superficial than the injection site. The device potentially having a multitude of said components (including but not limited to vials, plungers, gas cylinders, springs, needles, reservoirs, sheaths, shields, chambers, and/or retracting springs) in order to administer multiple medicaments into a patient at one time and/or at different times, as one dose and/or in multiple doses, depending on when each individual system is activated. The device can have selectors and/or other mechanisms to allow the user to choose which medicament to administer. Each individual system can comprise an activation mechanism (such as a spring and/or gas cylinder), a chamber within said housing, and a plunger, vial, reservoir, needle, and/or retraction spring; wherein upon exit of the desired contents of the vial, the entire needle, reservoir, vial, and/or plunger assembly retracts towards the proximal end of housing by some means such as a wire, spring, o-ring, and/or rubber membrane and/or a needle protection portion slides over the needle following delivery of the medicament.

Figure 21A:
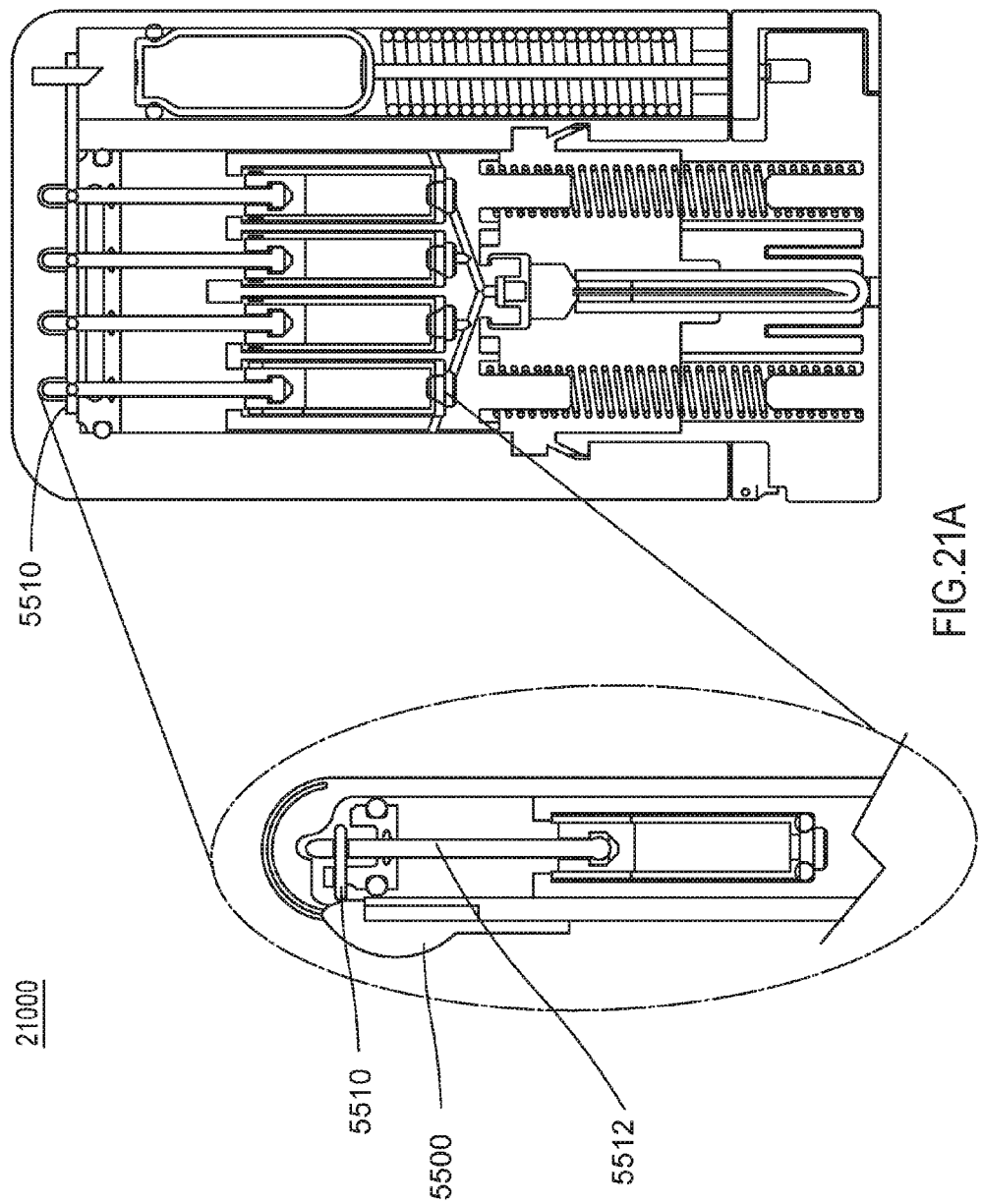
FIG. 21A is a cross-sectional view taken along lines A-A of FIG. 18A of an exemplary embodiment of a system 21000.
Figure 21B:
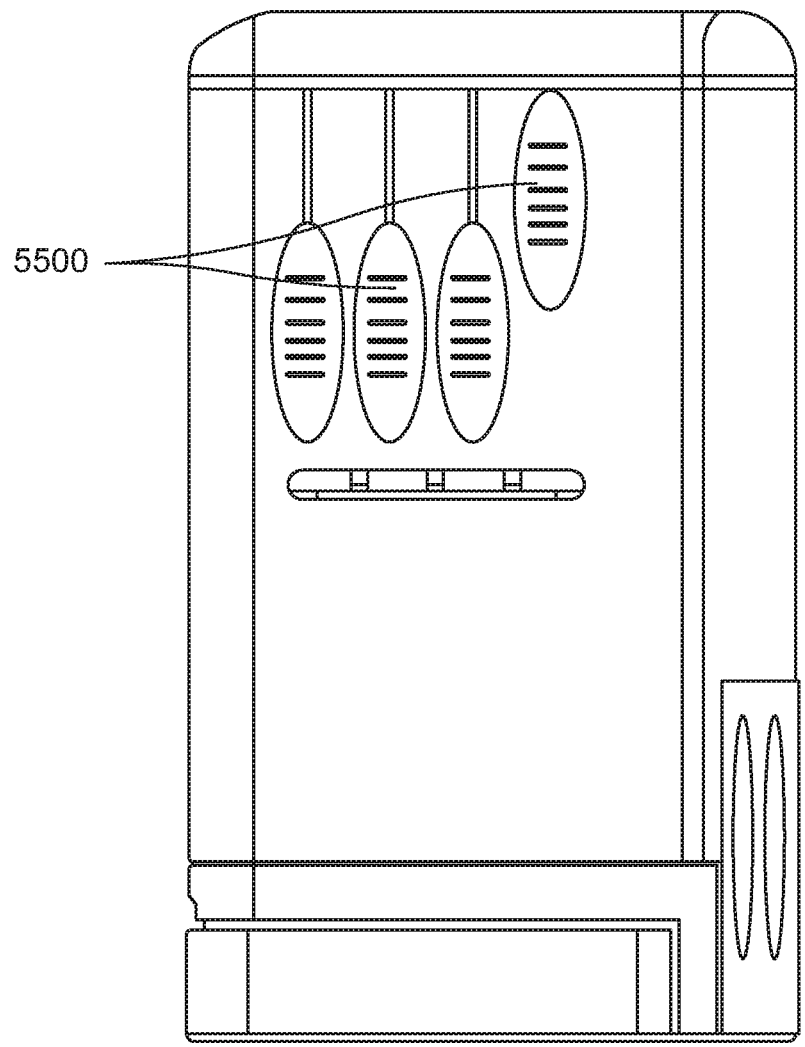
FIG. 21B is a front view of an exemplary embodiment of a system 21000.

A method for administering multiple pharmaceuticals is depicted in FIGS. 21A and 21B. The injector 21000 can include medicament selectors 5500 in order to allow the user to select which medicament to inject. The user can select the medicaments by sliding one or more selectors 5500 upward into their final position. An audible click or some other indicator may occur to alert the user to this final position. Moving the selector or multiple selectors upwards can allow a pin 5510 to snap into the plunger rod 5512 and/or into the pusher bar, which can create an entire portion that can push the vial system downwards and can inject the medication through the vial, the reservoir and/or needle. (This method can also be used with the Needleless injector method as described earlier in this document) Methods such as this embodiment could be extremely useful in applications for anti-nerve agents or pain therapies. The device 21000 can also include a resilient material, such as rubber, to seal the selector openings and that can also slide within the housing once the selector 5500 is pushed upward. Once the aforementioned pins 5510 are in place, the device can function and activate similarly to that described above. A safety mechanism can be modified to eliminate the sliding selectors from being prematurely pushed upwards.

Exemplary Embodiment Seven: The Wet/Dry Injector

This exemplary embodiment can comprise a compact auto-injector that can have the ability to mix two or more medicaments in either a liquid or powder form to create one injectable medicament. The novel component of this device can be considered to be the use of a plurality of vials to deliver the medicament. The device also can comprise a needle protection system.

An exemplary delivery system can comprise a housing, plurality of vials, plunger for each vial, a mixing activation mechanism, an activation chamber or vial, single needle or needle cannula, and/or a medicament or medicaments stored within each vial. Pre-injection, two or more medicaments can be stored separately in a vial and/or storage compartment and can communicate with each other once the mixing activation mechanism is initialized. The mixing activation mechanism could comprise a button, trigger, threaded rod, and or some other member that removes a piece or portion and/or punctures a piece or portion that is preventing each medicament to communicate with each other. The mixing activation mechanism may comprise a membrane, piece, and/or portion that may be removed pre-injection by the user in order to allow the separate vials and/or storage containers to communicate with each other. The mixing activation mechanism can be a piece that is manipulated in some way by the user in order to cause the contents of each compartment to mix with each other. This communication may occur by shaking the device and/or may occur automatically with the mixing activation mechanism. For instance, the mixing activation mechanism may cause each medicament to be released into an activation chamber, which may itself be a separate vial. This mixed medicament can be the medicament that will be injected into the patient. The delivery system further encompassing the mixed medicament vial or plurality of mixed medicament vials in communication with the plunger(s) at the proximal end of the housing and in communication with a reservoir that can contain a single needle or needle cannula at the distal end; the needle can be protected by some sheath/shield; the housing can further comprise a passage that is also in communication with the proximal end of the plunger such that when the spring(s) is activated from the distal or proximal end, a force can be applied through the passage on the plunger at the proximal end allowing for the plunger(s), vial(s), reservoir, and/or needle to travel towards the distal end of the housing; wherein the force provided can be caused by a spring, bar, contents from a gas cylinder, and/or other force mechanism; wherein the plunger can slideably travel through the vial towards the distal end to allow for the appropriate dose of medicament to be delivered; upon exit of the desired contents of the vial, the entire needle, reservoir, vial, and/or plunger assembly can retract towards the proximal end of housing by some means such as a wire, spring, o-ring, and/or rubber membrane and/or a needle protection portion slides over the needle following delivery of the medicament.

Figure 22A:
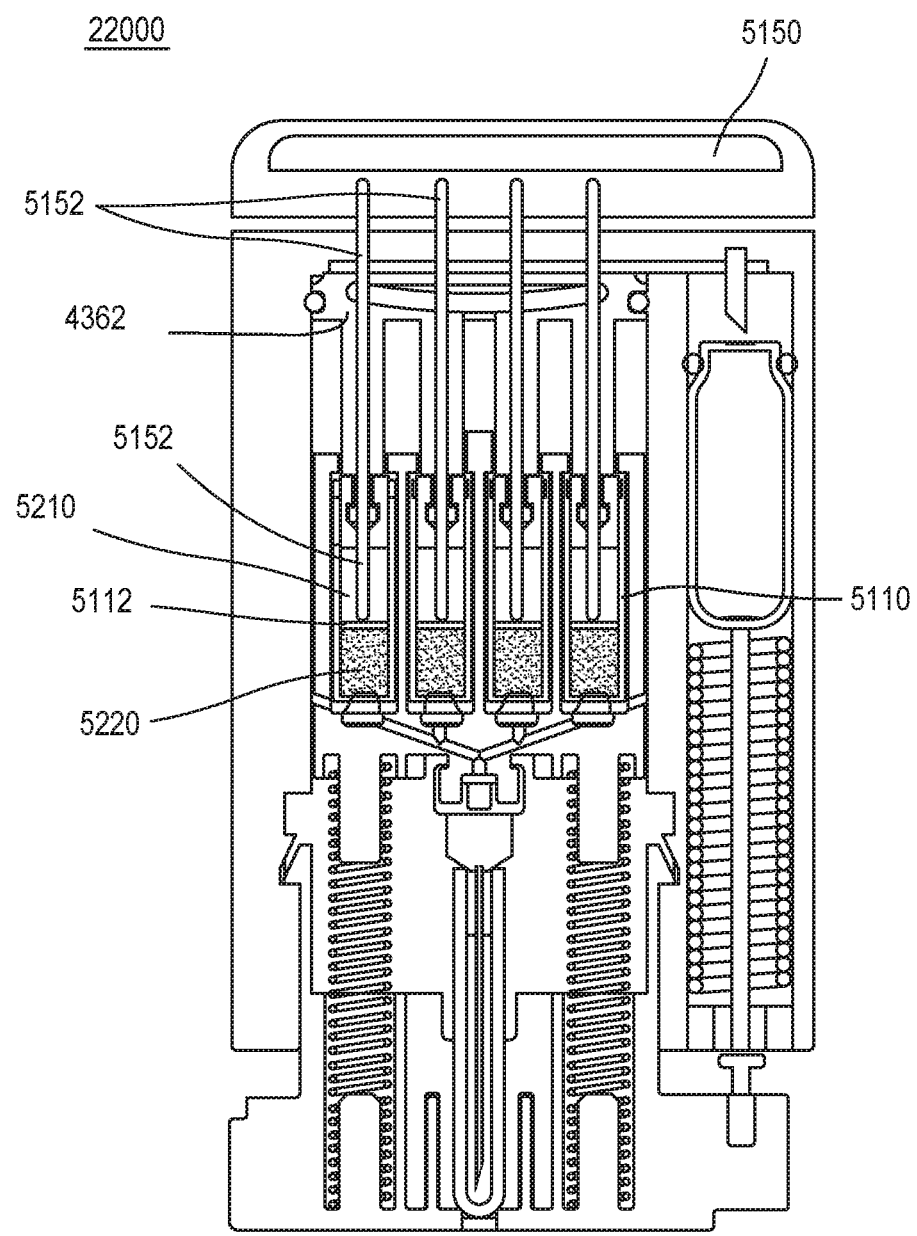
FIG. 22A is a cross-sectional view taken along lines A-A of FIG. 18A of an exemplary embodiment of a system 22000.
Figure 22B:
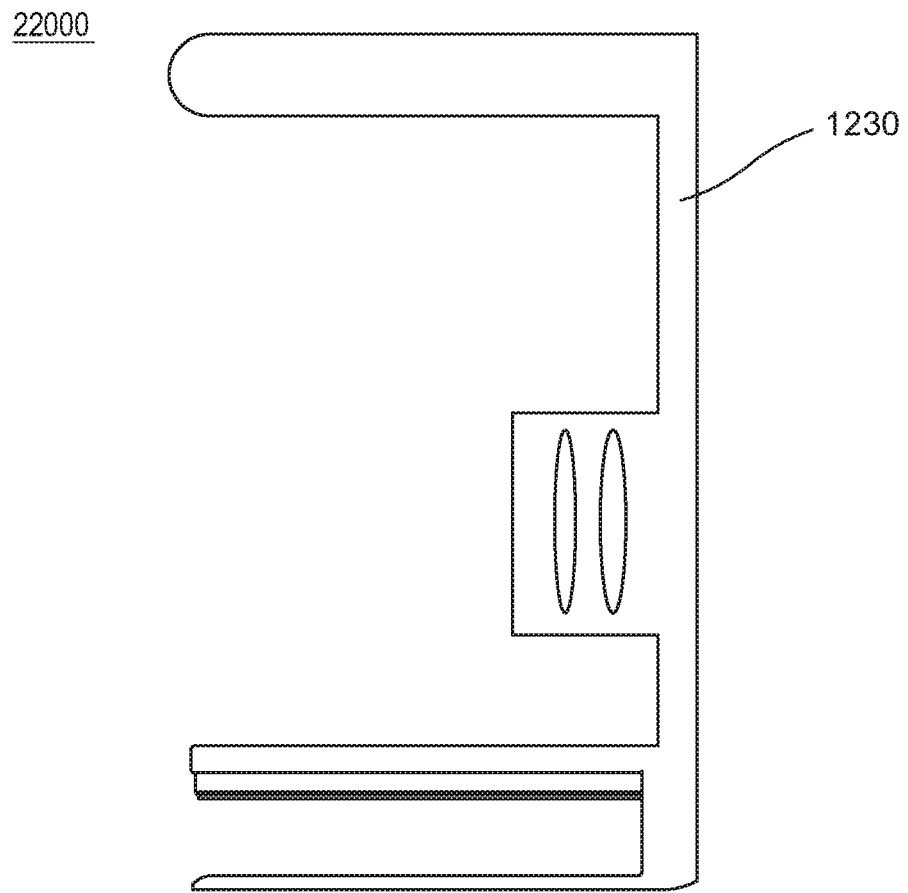
FIG. 22B is a front view of an exemplary embodiment of a system 22500.

FIGS. 22A and 22B depict a novel method for injecting lyophilized medications, and/or powdered biologics that could need to be reconstituted pre-injection. FIG. 22A shows a mechanism to mix and/or create an injectable medicament from two or more separate aforementioned substances. The figure depicts multiple vials 5110 that could have two substances in each vial separated by a pierceable membrane 5112 and/or other frangible piece. The vials in this embodiment can have one wet substance 5210 (such as sterilized water) and one dry substance 5220 (such as glucagon powder). The user can take off the safety tab 1230, which can prevent the user from accidental injection and/or premature activation of the device. Once the safety device 1230 is removed, the user can twist and/or rotate the twisting portion 5150 at the top of the housing. By rotating this top portion, the rods 5152 attached to this portion (which can be threaded rods) can move downward. These rods 5152 can be located in the vials 5110 and/or through the pusher bar 4362. The rods 5152 can have a sharp piercing portion on the distal end which can aid in puncturing the aforementioned pierceable membrane 5112 that can separate the substances in the vial. Once the piercing rod 5152 punctures the frangible and/or pierceable membrane, the substances can mix together to form one medicament. The user can also shake the entire housing in order to aid in this mixing process Exemplary Embodiment Eight: Needle-End Safety System Certain exemplary embodiments can comprise a safety system that can allow a user to remove some cap, bar, lock at the same end of an auto-injector housing where the needle is located. This can allow the device to be ready for activation while still protecting the needle at the same time. Many auto-injectors, such as most pen-like injectors, have the activation safety mechanism on the opposite end of where the needle is located. In an emergency situation, the user may mistake this safety cap as protecting the needle, when in fact this is not the case. There have been many documented cases of digital injection into a user's thumb or finger because of this reason. Having the safety mechanism at the same end of the needle can eliminate this risk.

Exemplary Embodiment Nine: Auto-Injector with Feedback

The use of auto-injectors and drug delivery systems is common in the medical industry. Auto-injectors can deliver a range of medicaments into a patient, ranging from chronic therapies to critical care injectables. As more therapies are developed, the need for a vehicle to deliver these therapies is ever-increasing. Certain auto-injectors currently on the market can lack attributes that can allow the user to understand the device's functionality and/or operation. Thus, there is perceived a need for an auto-injector that can provide audible, haptic, and/or visual feedback to the user in order to effectively train and/or guide the user on how to properly operate the auto-injector and/or to mitigate user-related hazards that could occur when the device is not used correctly.

The incidence of use-related hazards associated with auto-injectors is increasing. Common problems associated with certain injectors on the market include poor design, sharps exposure, and poor instruction. Many auto-injectors on the market are in the form of an apparatus that resembles a pen or marker. The safety mechanism for most of these devices can cause patient confusion as it is often protecting the activation mechanism and not the location where the needle protrudes out of the device. There have been numerous cases of the user accidentally injecting the needle into their own thumb or finger because of this hazard. Examples of devices that incorporate this design can include certain pen-type auto-injectors for allergic emergencies, and/or certain anti-nerve agent auto-injectors currently supplied to both domestic and foreign militaries. These devices, and most auto-injectors on the market, also can allow the needle to remain protruding out after use, thereby potentially causing a post-injection sharps hazard. Further, many of these injectors exhibit poor instruction and/or labeling. Due to the cylindrical design of certain auto-injectors, the surface area for labeling can be small, rounded, and therefore can prevent a user from easily reading important information regarding the use of the device. For many injectors that are used in emergency situations, it can be important that the user be able to use the device correctly and efficiently. The user might not take or have time to read the instructions on the device during such a critical scenario.

For one or more of these reasons, an interactive auto-injector or medical device is described that can provide a user with visual, haptic, and/or audible feedback in order to mitigate the aforementioned risks and/or to allow for easy injection of medications.

Certain exemplary embodiments can provide an interactive auto-injector and/or a method of providing audible, haptic, and/or visual feedback to a user when operating the auto-injector. An auto-injector can be defined as any device that allows a user to deliver a medicament without having to manually prepare the injection. This can include pen delivered injectors, syringes, needleless injectors, gas powered auto-injectors, and/or any other auto-injector and/or medical device used to inject a pharmaceutical into a user/patient, etc.

Certain exemplary embodiments can provide an auto-injector that can comprise an information device and/or system comprising at least one sensor (e.g., a pressure sensor, proximity sensor, tactile sensor, and/or biometric input device, etc.), switch (e.g., gate switch, microswitch, and/or pushbutton, etc.), embedded system (e.g., microprocessor, memory, embedded operating system, system bus, input/output interface, and/or network interface, etc.), audible output sub-system (e.g., speaker, horn, buzzer, and/or piezoelectric transducer, etc.), visual output sub-system (e.g., flag, marker, light, liquid crystal display (LCD), light emitting diode (LED), optical fiber, organic polymer display, electric paper, screen, display, monitor, and/or tube, etc.), haptic output sub-system (e.g., buzzer, vibrator, bulging portion, tactile stimulator, cooler, and/or heater, etc.), and/or any other component and/or sub-system that would aid in providing audible, visual, and/or haptic feedback to a user of the auto-injector, along with appropriate circuitry, control system(s), housing(s), shielding, electrical conductors, and/or power source(s), etc.

Certain embodiments of auto-injectors can comprise a housing, safety mechanism, activation mechanism (such as a spring means or compressed gas cylinder), a vial or container for storing the medicament, and a needle for delivering the medicament. Certain exemplary embodiments can provide one or more audible, visual, and/or haptic outputs to guide and/or instruct the user how to use the auto-injector properly. Sensors and/or switches can be placed on the safety tab, on the bottom of the device where the needle comes out, and/or where the inner sleeve slides up to activate the device. Visual outputs can be placed at each of the aforementioned locations as well and/or instead. An audible output sub-system can be placed anywhere on the device for audible feedback. A haptic output sub-system can be placed anywhere on the device. These electronically-triggered and/or active components and/or subsystems can be incorporated into the labeling of the device and/or as a separate component to provide this visual, haptic, and/or audible feedback.

For example, the user can push a button or switch on the device to initiate the audible, haptic, and/or visual output sub-system. A pre-recorded audible voice can tell the user to pull up on the safety tab, while a visual and/or haptic output can be rendered on the safety tab to provide a visual and/or haptic clue to the user as to where the safety tab is located. Once the safety tab is pulled up correctly, a sensor or switch could trigger the next step for the voice to announce, for example, asking the user to place the base of the device on the outer portion of their thigh while also triggering a visual output to light the base of the device. By way of further example, the user can be provided a visual clue in which at least a portion of the base of the device is lighted and/or colored red, and/or the user can be provided a haptic clue in which the base on the device is moved and/or the base is heated sufficiently (such as to between approximately 105 degrees F. and approximately 120 degrees F., including all values and sub-ranges therebetween) to substantially warm, yet not burn, the user's skin. The embedded operating system, which can run in hard real-time to avoid delays that might be significant and/or life-threatening, can also recognize a failure to complete a step in a certain specific timeframe and cause the step to be repeated if necessary and/or provide negative feedback if the user fails to perform a step properly (e.g., via input from a sensor or switch, the operating system can timely notice that the device is not placed on the skin of the thigh correctly and can cause the audible output subsystem to tell the user to repeat the placement step). Once the user places the device on the thigh properly, the sensor or switch could trigger the next audible, visual, and/or haptic clue and/or output, such as asking the user to push down on the outside sleeve of the device with force. By instructing the user step-by-step through each task, user error and/or risks of certain hazards can be reduced and/or eliminated.

Certain exemplary embodiments can provide a compact, credit card-sized auto-injector used to deliver a variety of medicaments, such as pharmaceuticals and/or agents. Though this auto-injector can eliminate many problems associated with certain pen-style auto-injectors, such as the sharps hazard and/or the poor safety tab design, there can be a need for an interactive auto-injector in order to aid in user instruction of the device and/or to help ensure the device is used properly any and/or every time it is needed. The following, and the attached figures, further describes such an auto-injector.

Figure 23:
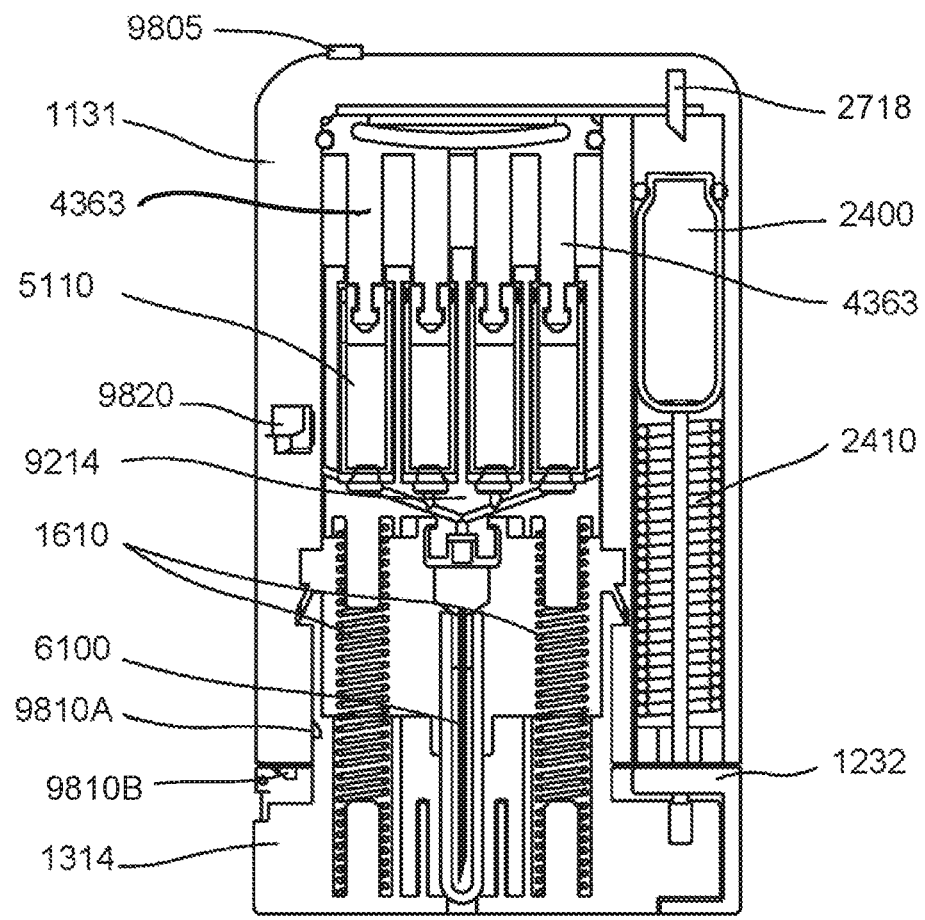
FIG. 23 is a cross-sectional view taken along lines A-A of FIG. 18A of an exemplary embodiment of a system 23000.

FIG. 23 portrays an auto-injector 23000 having a housing 1131 similar to the length and width of a credit card, an activation mechanism on one side and a vial system 5100 non-coaxial with the activation mechanism. The activation mechanism can comprise a compressed spring 2410 and compressed gas cylinder 2400 used as the force mechanism, and a puncturing mechanism 2718 to dispel the contents of the compressed gas cylinder 2400. A vial system 5100 can be comprised of a pusher bar 4363, plungers, vial(s)/medicament storage container(s), a reservoir 9214, a needle 6100, and a needle sheath. Retraction springs 1610 located at the base of the reservoir 9214 can push the needle 6100 back within the housing 1131 after injection. A slideable base 1314 can be used to activate the activation mechanism, which can be transparent to show the location of the aforementioned needle. A safety tab 1232 can be located between the base 1314 and the housing 1131 and/or can keep the activation mechanism from being activated while protecting the user from the needle 6100. Sensors 9810A, 9810B and/or switches, which can help trigger audible, haptic, and/or visual feedback, can be located on the base 1314 and/or on the safety tab 1232. A button 9805 and/or switch, which can help trigger audible, haptic, and/or visual feedback subsystem(s), can be located on the housing 131. The feedback sub-system(s) can be activated based on inputs received and/or interpreted by the embedded operating system.

For example, an audible output sub-system 9820 located in the housing 1131 can provide audible feedback to the user of the device. The audible output sub-system 9820 can be comprised of one or more piezoelectric transducers, small and/or large cones and/or speakers, sensors, capacitors, memories, power sources (e.g., battery, fuel cell, spring-actuated generator, etc.) housing, wires, and any other electronic components needed to provide recorded audible feedback to a user. The audible output sub-system 9820 can be activated by the aforementioned button 9805 or switch on the housing 1131. The speaker can provide instructions for how the device is used and/or certain medication requirements.

As another example, visual outputs can be located throughout the device, and/or on the base, safety tab, labeling, and/or housing to provide visual clues to the user. These visual outputs can be activated by the operating system once a sensor or switch is triggered. An LCD, optical polymer, LED, electric paper, and/or other form of display, monitor, and/or screen and/or other visual output can provide data to the user such as dosage amount, expiration date, instructions, Federal Drug Administration (FDA) requirements, and/or other labeling requirements, etc.

Figure 24:
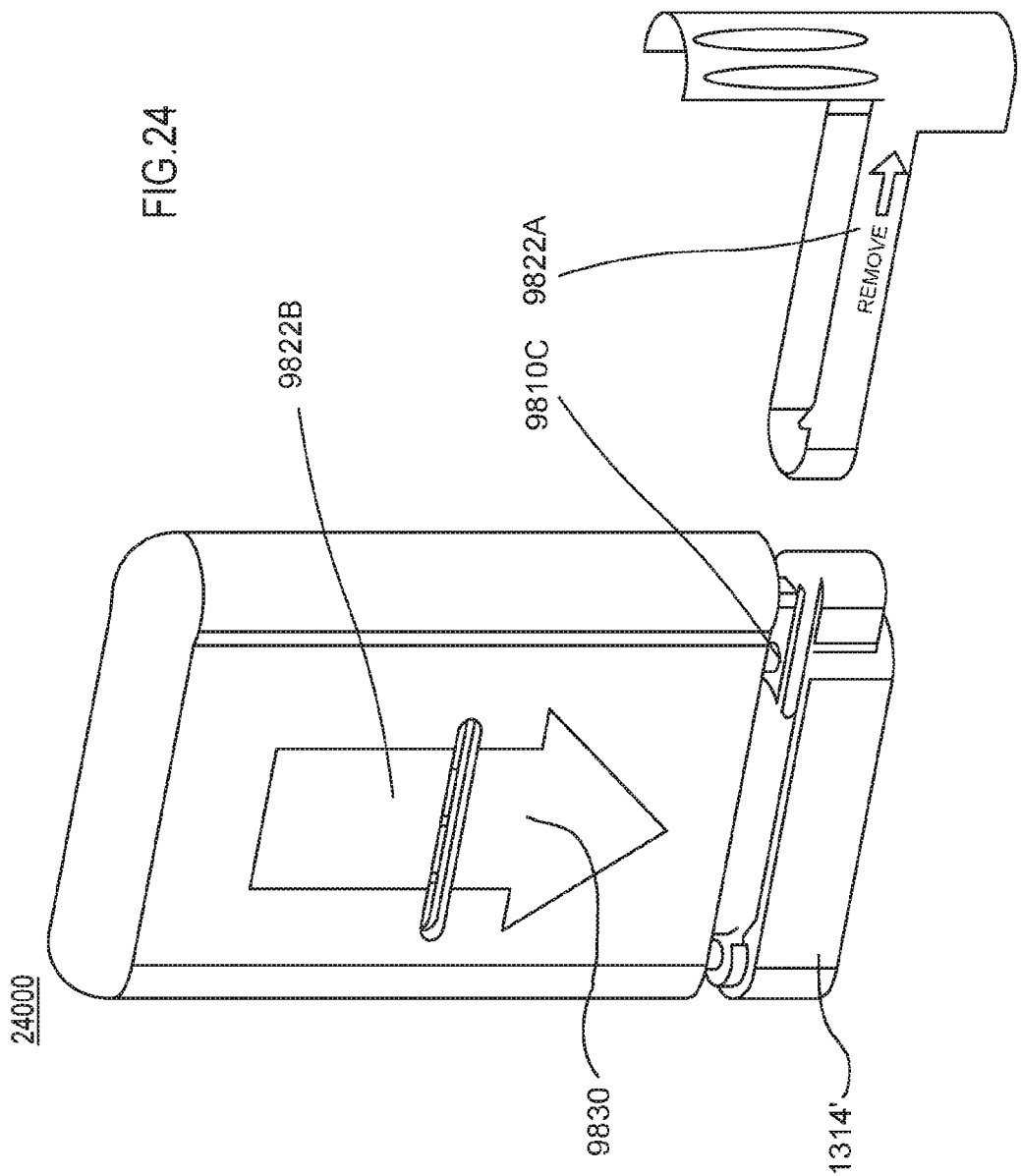
FIG. 24 is a perspective view of an exemplary embodiment an auto-injector 24000.
Figure 25:
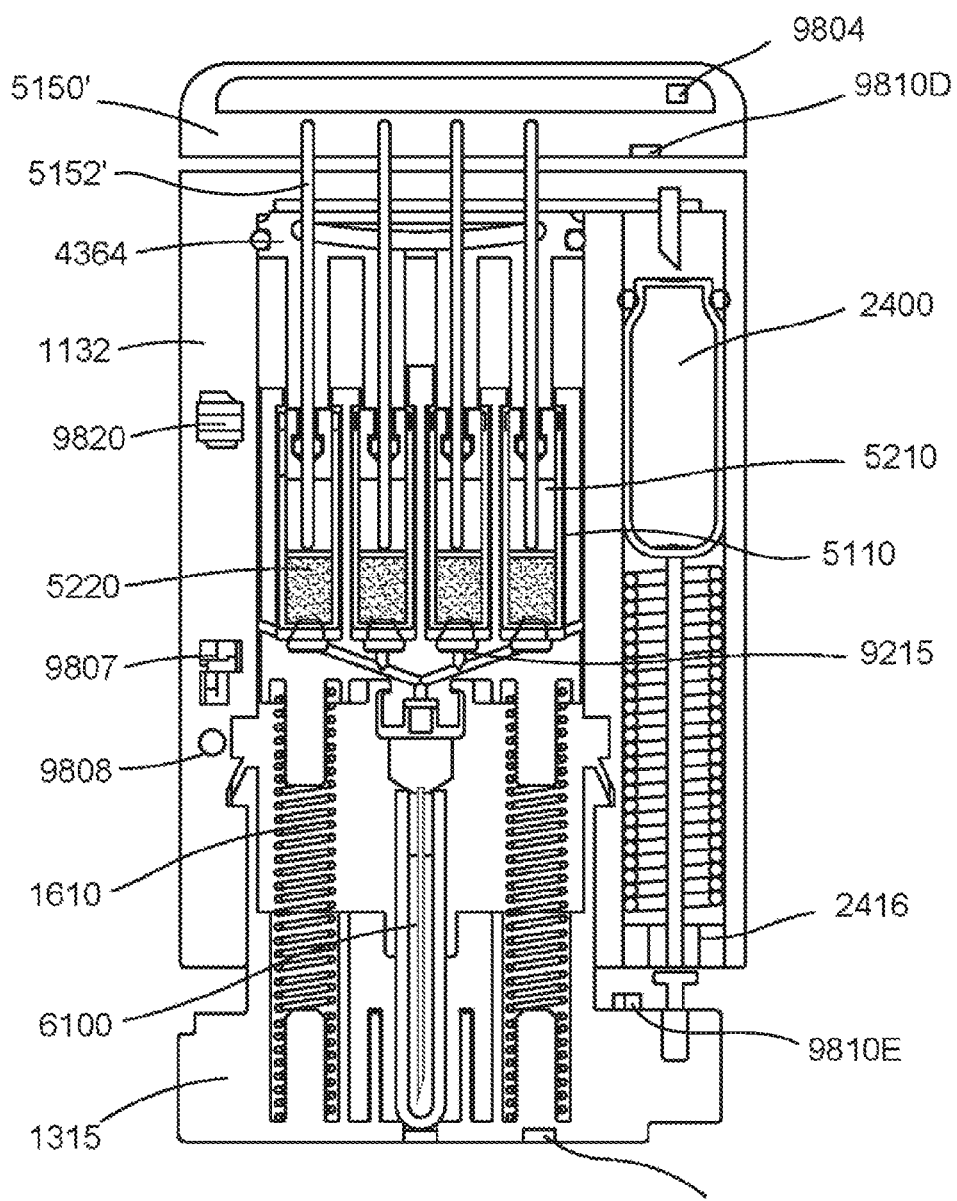
FIG. 25 is a perspective view of an exemplary embodiment an auto-injector 25000.

Referring to FIGS. 24 and 25, the user can push the button on the housing to, via the embedded processor, activate the audible, haptic, and/or visual feedback sub-system on the auto-injector. For example, a voice from the audible output sub-system (now activated) can provide an audible message to the user, such as "Please remove the safety tab." The safety tab 1232' can also light up from visual outputs 9822A located on the safety tab 1232'. Once the safety tab is removed, a sensor 9810C can be triggered that can also trigger the next audible task from the audible output sub-system 9820. The visual outputs (e.g. LEDs) 9822A and sensors (e.g., 9810C) activate the audible instructions for using the device, and to indicate key components of the device. If the safety tab 1232' is not removed within a certain timeframe, the first voice response can be repeated. The button or switch can be pressed several times or held in order to stop the process (in case the injector does not need to be used or the button was pressed accidentally). After the safety tab 1232' is removed, the next audible clue can be annunciated, such as "Please place the base of the device on the outer portion of your thigh." The base 1314' can simultaneously light up during this audible clue, providing a visual clue that demonstrates where the base is located and/or what portion of the base should be placed on the thigh. A sensor or switch, located on the base 1314', can be used to help determine if the auto-injector is placed correctly on the injection site. The same switch and/or sensor, and/or another switch and/or sensor located on the base 1314' can help trigger the next audible message, such as "Push down on the top of the device to activate the injector." That switch and/or sensor can also trigger one or more visual outputs 9822B to light up the labeling 9830 and/or an arrow pointing down toward the injection site (as shown in FIG. 24). The visual outputs (LEDs) 9822B with the label 9830 highlight placement of the injector and proper activation.

Certain exemplary embodiments can comprise a compact auto-injector that can have the ability to mix two or more medicaments, agents, solutes, solvents, etc., in either a liquid or powder form and/or create one injectable medicament. Certain exemplary embodiments can include an interactive system that can provide haptic, audible, and/or visual feedback to provide the user with instructions, hints, and/or clues in order to use the device properly. The auto-injector also can comprise a needle protection system.

An exemplary delivery system can comprise a housing, plurality of vials, plunger for each vial, a mixing activation mechanism, an activation chamber or vial, single needle or needle cannula, and/or a medicament or medicaments stored within each vial, etc. Prior to injection, two or more medicaments can be stored separately in a vial and/or storage compartment and can fluidically communicate with each other once the mixing activation mechanism is initialized. The mixing activation mechanism can comprise a button, trigger, threaded rod, and or some other member that removes a piece or portion and/or punctures a piece or portion that is preventing each medicament from communicating with each other. The mixing activation mechanism can comprise a membrane, piece, and/or portion that can be removed pre-injection by the user in order to allow the separate vials and/or storage containers to fluidically communicate with each other. The mixing activation mechanism can be a piece that is manipulated in some way by the user in order to cause the contents of each compartment to mix with each other. This communication can occur by shaking the device and/or can occur automatically with the mixing activation mechanism. For instance, the mixing activation mechanism can cause each medicament to be released into an activation chamber, which may itself can be a separate vial. This mixed medicament can be the medicament that will be injected into the patient.

The delivery system can comprise the mixed medicament vial or plurality of mixed medicament vials in mechanical and/or fluid communication with the plunger(s) at the proximal end of the housing and in mechanical and/or fluid communication with a reservoir that can contain a single needle or needle cannula at the distal end. The needle can be protected by a sheath and/or shield. The housing can comprise a passage that is also in mechanical and/or fluid communication with the proximal end of the plunger such that when the spring(s) is activated from the distal or proximal end, a force can be applied through the passage on the plunger at the proximal end allowing for the plunger(s), vial(s), reservoir, and/or needle to travel towards the distal end of the housing. The applied force can be caused by a spring, bar, contents from a gas cylinder, and/or other force mechanism. The plunger can slideably travel through the vial towards the distal end to allow for the appropriate dose of medicament to be delivered. Upon exit of the desired contents of the vial, the entire needle, reservoir, vial, and/or plunger assembly can retract towards the proximal end of housing by some means such as a wire, spring, o-ring, and/or rubber membrane and/or a needle protection portion slides over the needle following delivery of the medicament.

The interactive system can comprise a speaker sub-system that can comprise piezos and/or other components to produce audible sounds and/or human voice; a haptic sub-system that can provide haptic feedback to the user; a visual sub-system that can comprise light emitting diodes, LCD's, optical fibers, and/or other components that can produce visual outputs such as light and/or color; a processor that can be used to control the activation of such components; a power source such as a battery that can power the aforementioned interactive system; and/or switches, buttons, and/or sensors that can activate certain visual, haptic, and/or audible clues at a particular moment.

FIG. 25 depicts a novel method and device 25000 for injecting lyophilized medications, and/or powdered biologics that might need to be reconstituted pre-injection. FIG. 25 shows a mechanism to mix and/or create an injectable medicament from two or more separate aforementioned substances. FIG. 25 depicts multiple vials 5110 that can have, for example, at least two substances in each vial separated by one or more pierceable membranes and/or other frangible pieces. The vials 5110 can have at least one wet substance 5210 (such as sterilized water) and at least one dry substance 5220 (such as glucagon powder). The user can take off the safety tab, which can prevent the user from accidental injection and/or pre-mature activation of the device. Once the safety tab and/or device is removed, the user can twist and/or rotate the twisting portion 5150' at the top of the housing. By rotating this top portion, the rods 5152' attached to this portion (which can be threaded rods) can move downward. These rods 5152' can be located in the vials 5110 and/or through the pusher bar 4364. The rods 5152' can have a sharp piercing portion on the distal end which can aid in puncturing the aforementioned pierceable membrane(s) that can separate the substances in the vial 5110. Once the piercing rod punctures the frangible and/or pierceable membrane(s), the substances previously separated thereby can mix together to form one medicament. The user can also shake the entire housing 1132 in order to aid in this mixing process. The device 25000 includes an activation mechanism 2416, and delivers mixed medicament from the vials 5110 through the reservoir 9215 and to the needle 6100.

The device 25000 can include an electronic/interactive system to provide visual, haptic, and/or audible feedback to the user. This interactive system can include a microprocessor 9807 to control the specific feedback components, a speaker subsystem 9820, a haptic sub-system, a sub-system of switches and/or sensors (see switches and/or sensors 9810D. 9810E. 9810F) a subsystem of LEDs or optics, a battery power source 9808, and any other component needed to produce audible or visual outputs. FIG. 25 portrays these components located throughout the device; however, the actual placement of these components is flexible. The user can activate the interactive system by pushing a button 9804 or switch located on the housing 1132 of the device. This button 9804 or switch can activate the processor 9807 which can then send signals to the audible output sub-system, haptic output sub-system, and/or visual output sub-system. The audible output sub-system 9820 can provide an audible clue for the initial task, which can be in the form of a human, humanesque, and/or understandable voice stating, "Please remove the safety tab." A signal can also be sent simultaneously to the safety tab visual output (potentially one or more LEDs) to provide a visual light and/or color clue to the user as to where the safety tab is located. Once the safety tab is removed, a switch or sensor 9810E can send a signal to the processor 9807 and activate the next audible, haptic, and/or visual clue. This can be a human voice that states "Please twist the top portion of the injector to activate the mixing mechanism." As with the safety tab, an LED or some other visual clue then can be activated, lighting up the mixing activation mechanism 5150' and/or a haptic clue can be activated, such as vibrating, warming, cooling, bulging, moving, changing a texture of, etc., the mixing activation mechanism 5150'. A switch or sensor 9810D located near or on the mixing activation mechanism 5150' can be used to ensure that the mixing was complete and to trigger the next audible and/or visual clue by the processor. A voice next can state, "Please shake gently to mix the solution." After a certain amount of time, the processor 9807 then can send a signal to the audible output sub-system for the next task. This can be a voice that says, "Please place the injector on the outer portion of your thigh." A visual indicator of where the base/injector should be placed also can be simultaneously activated. A switch, sensor, or button 9810F then can recognize the correct placement of the device (and the base 1315) and trigger the next audible and visual clue. This can be a voice stating, "Push down on the top of the injector to activate the injection." Likewise, an arrow or some other visual and/or haptic clue can light up and/or be rendered to show the motion of how the injector should be pushed. The last clue can be an audible clue that states, "Hold in place for several seconds, remove, and dispose of properly," indicating that the injection is complete. Additional audible, haptic, and/or visual feedback subsystems can be used to provide the user with important information such as the expiration of the drug, improper use, and/or error. For instance, the device's LEDs or optics can blink, a display can render a message, a vibrator can vibrate, and/or an audible beep and/or voice can be activated after a particular time stamp is reached that corresponds to the expiration of the drug and/or device. As another example, once an auto-injector has been used, a message can be displayed describing proper disposal and/or recycling techniques.

Figure 26:
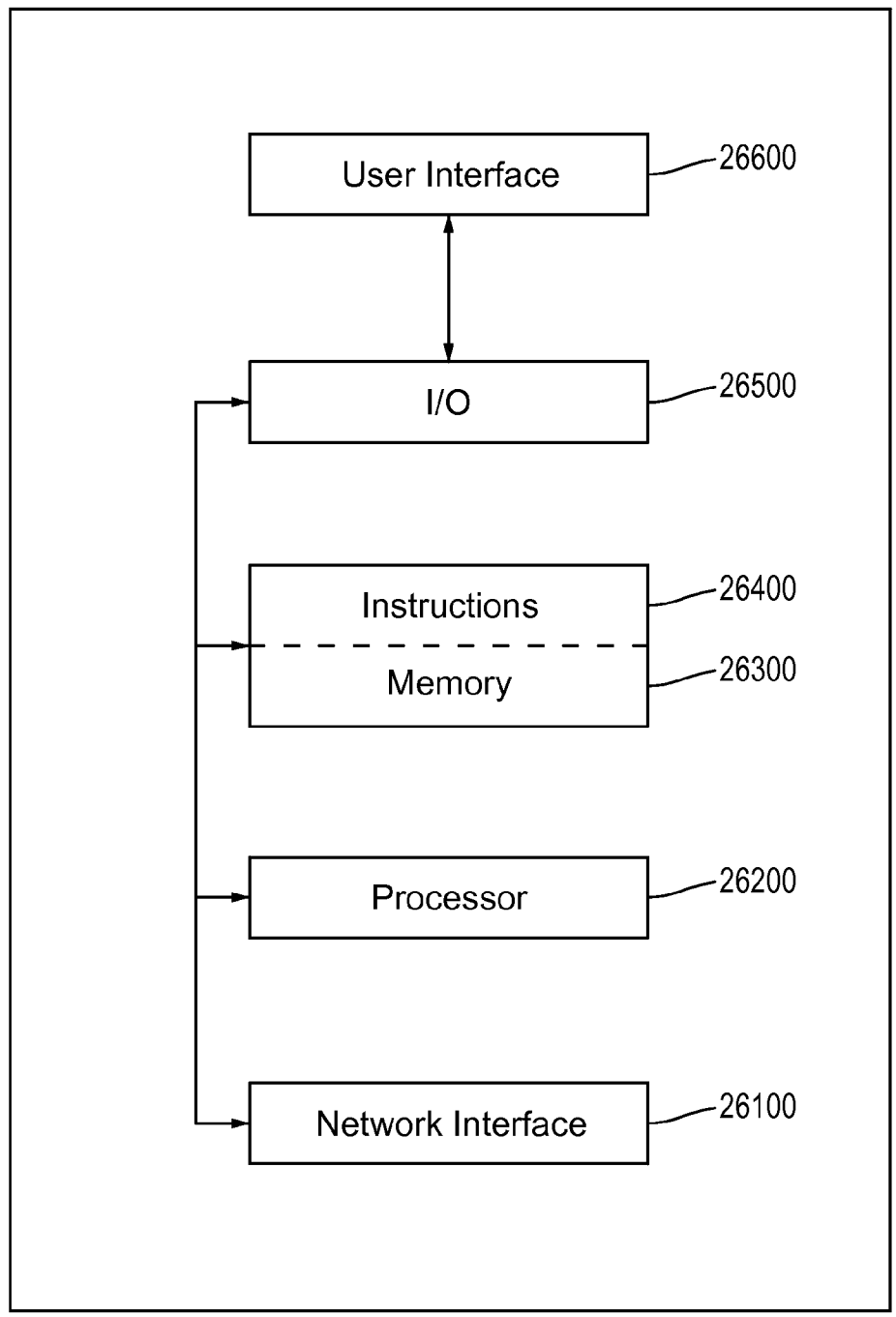
FIG. 26 is a block diagram of an exemplary embodiment an information device 26000.

FIG. 26 is a block diagram of an exemplary embodiment of an information system and/or device 26000, which in certain operative embodiments can comprise, for example, the interactive, integral, embedded, audible, haptic, and/or visual feedback system, such as described herein. Information system and/or device 26000 can comprise any of numerous components, such as for example, one or more network interfaces 26100, one or more processors 26200 running an embedded, real-time, hard real-time, and/or soft real-time operating system, one or more memories 26300 containing instructions 26400, one or more input/output (I/O) devices 26500, and/or one or more user interfaces 26600 coupled to I/O device 26500, etc.

In certain exemplary embodiments, via one or more user interfaces 26600, such as a graphical user interface, a user can view a rendering of information related to selecting, purchasing, obtaining, operating, maintaining, re-using, and/or disposing of an auto-injector. In certain exemplary embodiments, instructions 26400 can be modified and/or updated via replacing a removable memory 26300 and/or via replacing instructions 26400 (such as, e.g., via flashing an EEPROM, etc.). In certain exemplary embodiments, instructions 26400 can be modified and/or updated via downloading replacement instructions via network interface 26100. System 26000 can comprise a programmable logic controller.

Still other practical and useful embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application.

Thus, regardless of the content of any portion (e.g., title, field, background, summary, abstract, drawing figure, etc.) of this application, unless clearly specified to the contrary, such as via an explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

any elements can be integrated, segregated, and/or duplicated;

any activity can be repeated, performed by multiple entities, and/or performed in multiple jurisdictions; and any activity or element can be specifically excluded, the sequence of activities can vary, and/or the interrelationship of elements can vary.

Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all subranges therein. Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:
1. An apparatus, comprising:
a housing associated with an automatic injection device, the housing defining a status window;
a contact member movably coupled to a distal end portion of the housing, the contact member including a surface configured to be placed against a target location:
a movable member disposed within the housing;
an energy storage member disposed within the housing, the energy storage member configured to exert a force on the movable member to move the movable member within the housing to transition the apparatus from an initial configuration to an activated configuration;
an electronic circuit system coupled to the housing, the electronic circuit system including a switch and a speaker, the electronic circuit system configured to produce a recorded speech output when the switch is manipulated; and a use indicator configured to move within the housing along with the movable member between a first position and a second position, the use indicator configured to move from the first position to the second position when the contact member is in a fixed position relative to the housing, the use indicator providing a visual indication when the apparatus is in the activated configuration and the use indicator is in the second position.

2. The apparatus of claim 1, wherein:
the use indicator is in the first position when the apparatus is in the initial configuration, the use indicator being in the second position when the apparatus is in the activated configuration.

3. The apparatus of claim 1, wherein:
the use indicator exposes a colored portion indicating that the apparatus is in the activated configuration when the use indicator is in the second position.

4. The apparatus of claim 1, wherein the housing is the housing of an auto-injector, the apparatus further comprising:
a medicament container disposed within the housing, the medicament container including a medicament, the medicament being viewable through the status window when the apparatus is in the initial configuration,
the movable member configured to move within the medicament container to expel the medicament from the medicament container when the apparatus transitioned to the activated configuration.

5. The apparatus of claim 4, wherein:
the movable member is configured to expel the medicament via a needle in response to the force exerted by the energy storage member.

6. The apparatus of claim 1, wherein the energy storage member is a non-electronic energy storage member.

7. The apparatus of claim 1, wherein:
the movable member is piston; and
the use indicator is spaced apart from the piston.

8. The apparatus of claim 1, wherein
the recorded speech output identifies a location of the contact member and instructs a user to place the contact member against the target location.

9. The apparatus of claim 1, wherein the energy storage member is a non-electronic energy storage member and the contact member is configured to actuate the energy storage member when the contact member is moved relative to the housing, the apparatus further comprising:
a push button configured to actuate the electronic circuit system, the electronic circuit system configured to be actuated independently from the energy storage member.

10. The apparatus of claim 1, wherein:
the recorded speech output is a first recorded speech output;
the switch is a first switch; and
the electronic circuit system includes a second switch, the electronic circuit system configured to produce a second recorded speech output when the second switch is actuated, the first recorded speech output being different from the second recorded speech output.

11. An apparatus, comprising:
a housing associated with a medical injector, the housing defining a status window;
a container within the housing;

a movable member disposed within the housing, the movable member configured to receive a force to move a piston within the container from a first piston position to a second piston Position to transition the apparatus from an initial configuration to an activated configuration;

an electronic circuit system operably coupled to the housing, the electronic circuit system including a switch and an audible output device, the electronic circuit system configured to produce a plurality of recorded speech outputs associated with an injection event via the audible output device when the switch is actuated; and a use indicator configured to move within the housing along with the movable member between a first indicator position and a second indicator position, the use indicator spaced apart from the piston, at least a portion of a contents of the container being viewable through the status window when the use indicator is in the first indicator position, the use indicator providing a visual indication when the piston is in the second piston position and the use indicator is in the second indicator position.

12. The apparatus of claim 11, wherein:
the use indicator is in the first indicator position when the apparatus is in the initial configuration, the use indicator is in the second indicator position when the apparatus is in the activated configuration.

13. The apparatus of claim 11, wherein:
the use indicator exposes a colored portion indicating that the apparatus is in the activated configuration when the use indicator is in the second indicator position.

14. The apparatus of claim 11, wherein:
the container is a medicament container including a medicament, at least a portion of the medicament being viewable through the status window when the apparatus is in the initial configuration.

15. The apparatus of claim 11, further comprising:
a contact member movably coupled to a distal end portion of the housing, the contact member including a surface configured to be placed against a target location,
the use indicator configured to move with the movable member between the first indicator position and the second indicator position independent from movement of the contact member relative to the housing.

16. The apparatus of claim 11, wherein:
the electronic circuit system is configured to produce a predetermined sequence of electronic outputs, the sequence including the plurality of recorded speech outputs.

17. The apparatus of claim 11, further comprising:
a contact member movably coupled to a distal end portion of the housing, the contact member including a surface configured to be placed against a target location,
the recorded speech output identifies a location of the contact member and instructs a user to place the contact member against the target location.

18. A method, comprising:
actuating an electronic circuit system to output a recorded speech output, the electronic circuit system coupled to a housing associated with a medical injector, the recorded speech output associated with an injection event;
placing a contact member against a target location, the contact member movably coupled to a distal end portion of the housing; and actuating a non-electronic energy storage member within the housing to produce a force to move a movable member within the housing from a first position to a second position, a use indicator moving along with the movable member, after the actuating the non-electronic energy storage member, from a first indicator position to a second indicator position within the housing, the use indicator moving from the first indicator position to the second indicator position when the contact member is in a fixed position relative to the housing, the use indicator providing a visual indication when the use indicator is in the second position.

19. The method of claim 18, wherein:

the actuating the non-electronic energy storage member includes actuating the non-electronic energy storage member to produce the force to move a needle from a first needle position to a second needle position, the needle fluidically coupled to a medicament container disposed within the housing.

20. The method of claim 18, wherein:

the actuating the electronic circuit system includes manipulating a button coupled to the housing; and the actuating the non-electronic energy storage member includes manipulating an actuator coupled to an end portion of the housing, the manipulating the actuator being performed independently from the manipulating the button.

21. The method of claim 18, wherein the recorded speech output identifies a location of the contact member coupled to the housing and the target location.

22. The method of claim 18, wherein, the movable member moves a piston when the movable member moves from the first position to the second position;

the placing includes moving the contact member relative to the housing; and the use indicator is spaced apart from the piston.

23. The method of claim 18, wherein:

the movable member moves a piston within a container disposed within the housing when the movable member moves from the first position to the second position;

at least a portion of a contents of the container being viewable through a status window defined by the housing before the actuating the non-electronic energy storage member; and the use indicator is spaced apart from the piston.

24. The method of claim 18, wherein the housing is associated with an auto-injector, the recorded speech output and the visual indication training a user in the operation of the auto-injector.

* * * * *

UNITED STATES PATENT AND TRADEMARK OFFICE
CERTIFICATE OF CORRECTION

PATENT NO. : 9,724,471 B2
APPLICATION NO. : 14/244311
DATED : August 8, 2017
INVENTOR(S) : Evan T. Edwards et al.

Page 1 of 1

It is certified that error appears in the above-identified patent and that said Letters Patent is hereby corrected as shown below:

In the Specification

Column 1, Line 22: the phrase "Devices. Systems, and Methods" should be -- Devices, Systems, and Methods --

Column 19, Line 1: the phrase "vials and reservoir" should be -- vials 5100, and reservoir --

Column 24, Line 27: the phrase "the housing 131" should be -- the housing 1131 --

In the Claims

Column 29, Line 40 (Claim 7): the phrase "is piston" should be -- is a piston --

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*